US012637669B2

(12) United States Patent
Morin et al.

(10) Patent No.: US 12,637,669 B2
(45) Date of Patent: May 26, 2026

(54) TWO-DIMENSIONAL AND THREE-DIMENSIONAL MICROARRAY CELL CULTURES USING ELASTOMERIC ASSEMBLY SUBSTRATES

(71) Applicant: NUtech Ventures, Lincoln, NE (US)

(72) Inventors: Stephen Morin, Lincoln, NE (US); Ruiguo Yang, Lincoln, NE (US); Karla Perez-Toralla, Lincoln, NE (US); Mark Rose, Lincoln, NE (US); Angel Olivera-Torres, Lincoln, NE (US); John Kapitan, Lincoln, NE (US); Grayson Minnick, Lincoln, NE (US)

(73) Assignee: NUTECH VENTURES, Lincoln, NE (US)

( * ) Notice: Subject to any disclaimer, the term of this patent is extended or adjusted under 35 U.S.C. 154(b) by 998 days.

(21) Appl. No.: 17/840,815

(22) Filed: Jun. 15, 2022

(65) Prior Publication Data

US 2023/0015901 A1 Jan. 19, 2023

Related U.S. Application Data

(60) Provisional application No. 63/211,347, filed on Jun. 16, 2021.

(51) Int. Cl.
*C12N 11/04* (2006.01)

(52) U.S. Cl.
CPC .................................... *C12N 11/04* (2013.01)

(58) Field of Classification Search
CPC ...... C12N 11/08; C12N 11/04; C12N 5/0068; C12N 5/0625; C12N 5/0693; C12N 5/0696; C12N 2513/00; C12N 2533/40; C12N 2539/00; C12N 5/0062; C12M 21/08; C12M 33/00
See application file for complete search history.

(56) References Cited

U.S. PATENT DOCUMENTS

| | | | | |
|---|---|---|---|---|
| 9,415,369 B2 | 8/2016 | Moore et al. | | |
| 10,119,958 B2 | 11/2018 | Zhang et al. | | |
| 2022/0145361 A1* | 5/2022 | Frenz | .................. | C12Q 1/6841 |

FOREIGN PATENT DOCUMENTS

| | | |
|---|---|---|
| CA | 2639954 C | 2/2008 |

OTHER PUBLICATIONS

Perez-Toralla et al., Facile Production of Large-Area Cell Arrays Using Surface-Assembled Microdroplets. Adv. Sci. 2020, 7, 2000769. https://doi.org/10.1002/advs.202000769 (Year: 2020).*

Perez-Toralla et al., Supporting Information: Facile Production of Large-Area Cell Arrays Using Surface-Assembled Microdroplets. Adv. Sci. 2020, 7, 2000769. https://doi.org/10.1002/advs.202000769 (Year: 2020).*

Perez-Torres, Dr. Karla et al., "Facile Production of Large-Area Cell Arrays Using Surface-Assembled Microdroplets", *Advanced Science*, (2020).

(Continued)

*Primary Examiner* — Dean Kwak

(74) *Attorney, Agent, or Firm* — Gerald T. Gray; Leydig, Voit & Mayer, LTD.

(57) ABSTRACT

The invention provides a method for preparing an ordered cell-containing microarray, and a system for preparing an ordered cell-containing microarray.

16 Claims, 22 Drawing Sheets

(56) References Cited

OTHER PUBLICATIONS

Sun, Yingnan "Inkjet-Printing Patterned Chip on Sticky Superhydrophobic Surface for High-Efficiency Single-Cell Array Trapping and Real-Time Observation of Cellular Apoptosis" *ACS Publications* (2018).
Hsieh, Chin-Hsiung, "Patterned PDMS based cell array system: a novel method for fast cell array fabrication using laser sintering and the hydrophobicity of PDMS films", *Biomed Microdevices*, (2010).
Feng, Wenqian, "Droplet Microarrays: From Surface Patterning to High-Throughput Applications formation of droplet microarrays with designed geometry on chemically prepatterned surfaces", *Advanced Materials*, (2018).

* cited by examiner a Organoid-in-Gel ECM-Modified Hydrogel Network

| | Species | Role | Curing | MW (*Mn*) | Stiffness |
|---|---|---|---|---|---|
| b |  PEGDA | | Photo | >10 kDa | 0.200 - 100 kPa |
| c |  PEGDA | | | 5 kDa | |
| |  | | Chem. | 10-40 kDa | 100 - 500 Pa |
| |  R' = HG Core R = -Acrylate, -SH | | | 10-40 kDa | |
| d |  Acrylate-PEGm-NHS | | N/A | N/A | N/A |
| e |  Amino-PEGm-4Mal | | N/A | N/A | N/A |

TWO-DIMENSIONAL AND THREE-DIMENSIONAL MICROARRAY CELL CULTURES USING ELASTOMERIC ASSEMBLY SUBSTRATES

CROSS-REFERENCE TO RELATED APPLICATION

This application claims the benefit of priority to U.S. Provisional Patent Application No. 63/211,347, filed Jun. 16, 2021, which is hereby incorporated by reference in its entirety.

STATEMENT REGARDING FEDERALLY SPONSORED RESEARCH OR DEVELOPMENT

This invention was made with Government support under P20 GM113126 and P30 GM127200 awarded by the National Institutes of Health, and under CMMI1826135 and DMR1555356 awarded by the National Science Foundation. The Government has certain rights in this invention.

BACKGROUND

Patterning large-scale single-cell arrays enables high-throughput single cell analysis and facilitates in vitro studies of cell-cell communication (Zhang et al., *Proc. Natl. Acad. Sci. U.S.A.,* 111, 2948 (2014)). Several strategies have been developed to create arrays of cells on engineered substrates, including, for example, programmed stress fields, microfluidic processing, surface chemistry, topography, mechanics, and inkjet printing. These techniques provide an ability to pattern cells for a range of specific applications/studies (e.g., tissue engineering and drug screening), where the appropriate technique is selected based on requirements such as cell count, array resolution, and size.

For instance, active patterning techniques, such as the use of optical (Xin et al., *Adv. Funct. Mater.,* 25, 2816 (2015)) and magnetic (Ino et al., *Lab Chip,* 8, 134 (2008)) tweezers, dielectrophoresis (Mittal, et al., *Lab Chip,* 7, 1146 (2007)), or surface acoustic waves (Collins et al., *Nat Commun,* 6, 8686 (2015)) can be used to position single cells for the generation of ordered, high resolution arrays of cells over small areas (Guo et al., *Proc. Natl. Acad. Sci. U.S.A,* 112, 43 (2015)). While these techniques may offer single-cell resolution and dynamic micromanipulation capabilities, they often require specialized equipment and localized hot spots are possible when external fields are used.

Applications that do not necessarily require single cell resolution have benefited from a set of well-established passive techniques, which rely on the use of micropatterned surfaces with chemical or topographical contrast, such as those generated using photolithography, plasma oxidation (Bretagnol et al., *Plasma Processes Polym.,* 3, 443 (2006)), or microcontact printing (Théry et al., *Nat. Cell Biol.,* 7, 947 (2005)) to achieve selective cell attachment, where the size and shape of the cell arrays are controlled at the micro/nanoscale. While these methods are useful for applications where scalability and process flexibility are priorities, they often do not have the same level of dynamic control or reconfigurability as field driven methods (Théry, *J. Cell Sci.,* 123, 4201 (2010)).

Stencil-based techniques, which can be considered a variant of the aforementioned passive microprinting methods, are similarly useful to applications where scalability and process simplicity are more important than single-cell resolution. Stencils, which are typically fabricated from thin polymeric membranes, have been used to create custom shaped colonies and a variety of cell array configurations (Ostuni et al., *Langmuir,* 16, 7811 (2000) and Wu et al., *Lab Chip,* 18 (2018)). However, stencil-based techniques can further require efforts to mitigate unwanted residue on the substrates after stencil removal and to minimize cell damage during stencil removal.

Another set of methodologies make use of droplets to encapsulate cells and pattern cell arrays by using inkjet printing technologies. Using this approach, cell-loaded microdroplets are deposited using inkjet printers enabling the generation of cell arrays with single cell resolution (Abate et al., *Proc. Natl. Acad. Sci. U.S.A.,* 107, 19163 (2010), Cole et al., *Proc. Natl. Acad. Sci. U.S.A.,* 114, 8728 (2017), Lan et al., *Nat. Biotechnol.,* 35, 640 (2017), and Lan et al., *Nat Commun,* 7, 1 (2016)). However, the serial nature of one-by-one droplet delivery has introduced new challenges associated with droplet evaporation during the time required to print the array (Liberski et al., *Acs Combinatorial Science,* 13, 190 (2011)).

Thus a need remains for a cell patterning technique, which combines the dynamic, single-cell resolution provided by field-based approaches while providing a scalable method for the preparation of large-area arrays. The invention provides a scalable method of preparing microarray cell cultures with single-cell resolution. These and other advantages of the invention, as well as additional inventive features, will be apparent from the description of the invention provided herein.

BRIEF SUMMARY

In a first aspect, the invention provides a method for preparing an ordered (e.g., patterned) cell-containing microarray, the method comprising process (A) or process (B):

(A) (i) providing an elastomeric substrate,
- (ii) modifying a surface of the elastomeric substrate to provide (i.e., produce) a surface-modified elastomeric substrate,
- (iii) spraying (i.e., discharging, dispensing, etc.) a cell-containing composition onto the surface-modified elastomeric substrate to provide (i.e., produce) a disordered cell-containing microarray, and
- (iv) applying a strain to the disordered cell-containing microarray to provide (i.e., produce) the ordered (e.g., patterned) cell-containing microarray.

(B) (i) providing an elastomeric substrate,
- (ii) modifying a surface of the elastomeric substrate to provide (i.e., produce) a surface-modified elastomeric substrate,
- (iii) applying a strain to the surface-modified elastomeric substrate to provide (i.e., produce) a strained surface-modified elastomeric substrate,
- (iv) spraying (i.e., discharging, dispensing, etc.) a cell-containing composition onto the strained surface-modified elastomeric substrate to provide (i.e., produce) a disordered cell-containing microarray, and
- (v) relaxing the disordered cell-containing microarray to provide (i.e., produce) the ordered (e.g., patterned) cell-containing microarray.

In a second aspect, the invention provides a method for preparing an ordered (e.g., patterned) cell-containing microarray, the method comprising process (A) or process (B):

(A) (i) providing an elastomeric substrate, (ii) modifying a surface of the elastomeric substrate to provide (i.e., produce) a surface-modified elastomeric substrate, (iii) spraying (i.e., discharging, dispensing, etc.) a cell-containing composition onto the surface-modified elastomeric substrate to provide (i.e., produce) a disordered cell-containing microarray, (iv) applying a strain to the disordered cell-containing microarray to provide (i.e., produce) the ordered (e.g., patterned) cell-containing microarray, and (v) attaching the cell-containing composition to the surface-modified elastomeric substrate in the ordered (e.g., patterned) cell-containing microarray by chemically, thermally, and/or photolytically treating the surface-modified elastomeric substrate in the ordered (e.g., patterned) cell-containing microarray.

(B) (i) providing an elastomeric substrate, (ii) modifying a surface of the elastomeric substrate to provide (i.e., produce) a surface-modified elastomeric substrate, (iii) applying a strain to the surface-modified elastomeric substrate to provide (i.e., produce) a strained surface-modified elastomeric substrate, (iv) spraying (i.e., discharging, dispensing, etc.) a cell-containing composition onto the strained surface-modified elastomeric substrate to provide (i.e., produce) a disordered cell-containing microarray, (v) relaxing the disordered cell-containing microarray to provide (i.e., produce) the ordered (e.g., patterned) cell-containing microarray, and (vi) attaching the cell-containing composition to the surface-modified elastomeric substrate in the ordered (e.g., patterned) cell-containing microarray by chemically, thermally, and/or photolytically treating the surface-modified elastomeric substrate in the ordered (e.g., patterned) cell-containing microarray.

In a third aspect, the invention provides a system for preparing an ordered (e.g., patterned) cell-containing microarray comprising a means for spraying a cell-containing composition and a means for mechanically straining an elastomeric substrate.

In a fourth aspect, the invention provides a system for preparing an ordered (e.g., patterned) cell-containing microarray comprising a means for spraying a cell-containing composition, a means for mechanically straining an elastomeric substrate, and a light source.

BRIEF DESCRIPTION OF THE DRAWINGS

FIG. 15B provides a zoom-in view of the white box shown in FIG. 15A.

DETAILED DESCRIPTION

Figure 1:
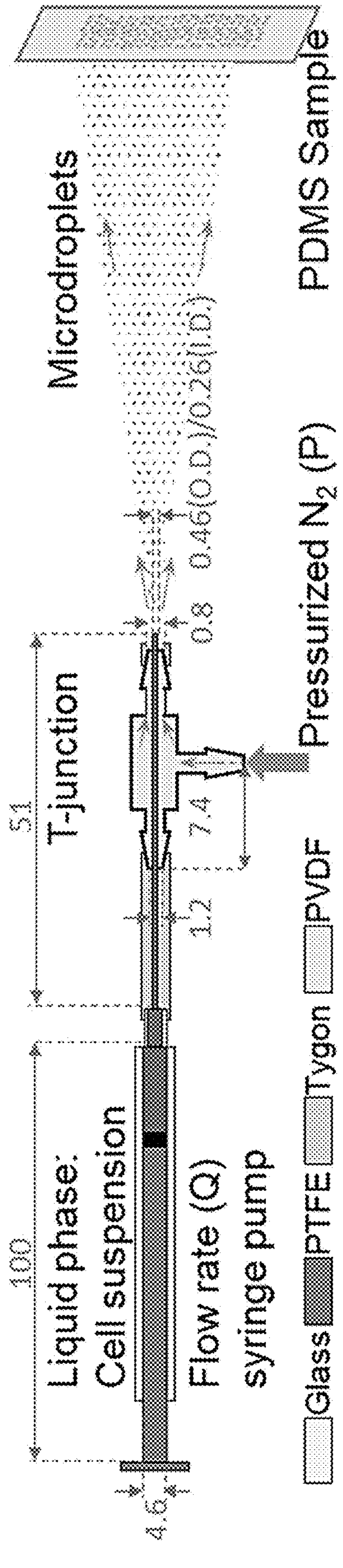
FIG. 1 provides an illustration of the droplet generation process including an exemplary nozzle design.

The present disclosure provides a method for preparing an ordered (e.g., patterned) cell-containing microarray. More particularly, the present disclosure provides a method for preparing an ordered (e.g., patterned) two-dimensional microarray (i.e., a micro-assembly of cells-in-droplets (μACD)) or an ordered (e.g., patterned) three-dimensional microarray (i.e., a micro-assembled organoids-in-gels (mAOG)).

Definitions

As used herein, the terms "ordered" and "patterned" can be used interchangeably and each refer to an organized arrangement having distinct sections or a specific image or design.

As used herein, the term "disordered" refers to a random arrangement that has no apparent design or organized arrangement.

As used herein, the term "microarray" refers to a two-dimensional or three-dimensional array on an elastomeric substrate, which comprises biological material (e.g., cells).

As used herein, the terms "spraying," "discharging," and "dispensing" can be used interchangeably and each refer to the process of applying droplets (e.g., aerosolized droplets) described herein to an elastomeric surface.

As used herein, the terms "elastomer," "elastomeric," or "elastomeric material" can be used interchangeably and refer a polymeric material that is elastic. Generally, the polymeric material is lightly cross-linked and amorphous with a glass transition temperature well below room temperature. Typically, the elastomeric material has a low Young's modulus and very high elongation at break when compared with other polymers.

As used herein, the terms "suspension media" and "cell suspension media" can be used interchangeably and refer to a cell media adapted for suspending a culture, for example, in a matrix. The suspension media can be particularly useful for cell lines that are nonadhesive (e.g., hematopoietic).

As used herein, the terms "culture media" and "cell culture media" can be used interchangeably and refer to cell media comprising an appropriate source of energy and compounds which regulate the cell cycle. For example the culture media can be composed of a complement of amino acids, vitamins, inorganic salts, glucose, and serum as a source of growth factors, hormones, and attachment factors.

As used herein, the term "gel media" refers to a synthetic crosslinked polymer capable of suspending a cell culture.

As used herein, the term "gel media precursor" refers to the liquid precursor used to form the gel media. The gel media precursor is capable of being sprayed (i.e., discharged, dispensed, etc.) in accordance with the invention described herein.

As used herein, the term "hydrogel" refers to a cross-linked hydrophilic polymer that does not dissolve in water. An exemplary hydrogel is Matrigel™ Matrix commercially available from Corning (Glendale, Arizona).

As used herein, the term "hydrogel precursor" refers to the liquid precursor used to form the hydrogel. The hydrogel precursor is capable of being sprayed (i.e., discharged, dispensed, etc.) in accordance with the invention described herein.

As used herein, the term "two-dimensional microarray" refers to a process of culturing cells on a flat surface (e.g., elastomeric surface), where the cells are adhered to the surface (e.g., elastomeric surface).

As used herein, the term "three-dimensional microarray" refers to a process of culturing cells in a scaffold, matrix, or suspension, which has been attached to a flat surface (e.g., elastomeric surface). The three-dimensional microarray facilitates the growth of three-dimensional cellular structures.

As used herein, the term "alkyl" refers to a straight or branched aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{1-12}$, $C_{1-14}$, $C_{1-16}$, $C_{1-18}$, $C_{1-20}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 30 carbons atoms, such as, but not limited to heptyl, octyl, nonyl, decyl, etc. Alkyl groups can be substituted or unsubstituted.

As used herein, the term "heteroalkyl" refers to an alkyl group as described herein, wherein one or more carbon atoms are optionally and independently replaced with a heteroatom selected from N, O, S, P, and Si.

As used herein, the term "alkenyl" refers to a straight or branched aliphatic radical having the number of carbon atoms indicated, the aliphatic radical having at least one olefin (i.e., double bond). Alkenyl can include any number of carbons, such as $C_{2-3}$, $C_{2-4}$, $C_{2-5}$, $C_{2-6}$, $C_{2-7}$, $C_{2-8}$, $C_{2-9}$, $C_{2-10}$, $C_{2-12}$, $C_{2-14}$, $C_{2-16}$, $C_{2-18}$, $C_{2-20}$, $C_{3-4}$, $C_{3-5}$, $C_{3-6}$, $C_{4-5}$, $C_{4-6}$ and $C_{5-6}$. For example, $C_{2-6}$ alkenyl includes, but is not limited to, ethylenyl, propylenyl, isopropylenyl, butylenyl, isobutylenyl, sec-butylenyl, pentylenyl, isopentylenyl, hexylenyl, etc. Alkenyl can also refer to alkenyl groups having up to 30 carbons atoms, such as, but not limited to heptylenyl, octylenyl, nonylenyl, decylenyl, etc. Alkenyl groups can be substituted or unsubstituted.

As used herein, the term "heteroalkenyl" refers to an alkenyl group as described herein, wherein one or more carbon atoms are optionally and independently replaced with a heteroatom selected from N, O, S, P, and Si.

As used herein, the term "alkynyl" refers to a straight or branched aliphatic radical having the number of carbon atoms indicated, the aliphatic radical having at least one triple bond. Alkynyl can include any number of carbons, such as $C_{2-3}$, $C_{2-4}$, $C_{2-5}$, $C_{2-6}$, $C_{2-7}$, $C_{2-8}$, $C_{2-9}$, $C_{2-10}$, $C_{2-12}$, $C_{2-14}$, $C_{2-16}$, $C_{2-18}$, $C_{2-20}$, $C_{3-4}$, $C_{3-5}$, $C_{3-6}$, $C_{4-5}$, $C_{4-6}$ and $C_{5-6}$. For example, $C_{2-6}$ alkenyl includes, but is not limited to, ethynyl, propynyl, butynyl, pentynyl, hexynyl, etc. Alkynyl can also refer to alkynyl groups having up to 30 carbons atoms, such as, but not limited to heptynyl, octynyl, nonynyl, decynyl, etc. Alkynyl groups can be substituted or unsubstituted.

As used herein, the term "heteroalkynyl" refers to an alkynyl group as described herein, wherein one or more carbon atoms are optionally and independently replaced with a heteroatom selected from N, O, S, P, and Si.

As used herein, the term "cycloalkyl" refers to a saturated or partially unsaturated, monocyclic, fused bicyclic, or bridged polycyclic ring assembly containing from 3 to 12 ring atoms, or the number of atoms indicated. Cycloalkyl groups can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, and $C_{3-10}$. Saturated monocyclic carbocyclic rings include, for example, cyclopropyl, cyclobutyl, cyclopentyl, cyclohexyl, and cyclooctyl. Saturated bicyclic and polycyclic carbocyclic rings include, for example, norbornane, [2.2.2] bicyclooctane, decahydronaphthalene and adamantane. Carbocyclic groups can also be partially unsaturated, having one or more double or triple bonds in the ring. Representative carbocyclic groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene.

As used herein, the term "heterocycloalkyl" refers to a cycloalkyl group as described herein, wherein one or more carbon atoms are optionally and independently replaced with a heteroatom selected from N, O, S, P, and Si.

As used herein, the term "aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can include any number of carbons, such as $C_{6-10}$, $C_{6-9}$, $C_{6-8}$, $C_{6-7}$, $C_{7-10}$, and $C_{8-10}$. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl.

As used herein, the term "heteroaryl" refers to an aryl group as described herein, wherein one or more carbon atoms are optionally and independently replaced with a heteroatom selected from N, O, S, P, and Si.

As used herein, the term "arylalkyl" refers to a group comprising any combination of "aryl" and "alkyl" groups described herein.

As used herein, the term "heteroarylalkyl" refers a groups comprising any combination of "alkyl", "aryl", "heteroalkyl", and "heteroaryl" groups described herein.

As used herein, the term "substituted" can mean that one or more hydrogens on the designated atom or group (e.g., substituted alkyl group) are replaced with another group provided that the designated atom's normal valence is not exceeded. For example, when the substituent is oxo (i.e., =O), then two hydrogens on the atom are replaced. Substituent groups can include one or more of a hydroxyl, an amino (e.g., primary, secondary, or tertiary), an aldehyde, a carboxylic acid, an ester, an amide, a ketone, nitro, an urea, a guanidine, cyano, fluoroalkyl (e.g., trifluoromethane), halo (e.g., fluoro), aryl (e.g., phenyl), heterocyclyl or heterocyclic group (i.e., cyclic group, e.g., aromatic (e.g., heteroaryl) or non-aromatic where the cyclic group has one or more heteroatoms), oxo, or combinations thereof. Combinations of substituents and/or variables are permissible provided that the substitutions do not significantly adversely affect synthesis or use of the compound.

Method for Preparing an Ordered Cell-Containing Microarray

In a first aspect, a method for preparing an ordered (e.g., patterned) cell-containing microarray includes process (A) or process (B):

(A) (i) providing an elastomeric substrate,
- (ii) modifying a surface of the elastomeric substrate to provide (i.e., produce) a surface-modified elastomeric substrate,
- (iii) spraying (i.e., discharging, dispensing, etc.) a cell-containing composition onto the surface-modified elastomeric substrate to provide (i.e., produce) a disordered cell-containing microarray, and
- (iv) applying a strain to the disordered cell-containing microarray to provide (i.e., produce) the ordered (e.g., patterned) cell-containing microarray, or (B) (i) providing an elastomeric substrate, (ii) modifying a surface of the elastomeric substrate to provide (i.e., produce) a surface-modified elastomeric substrate, (iii) applying a strain to the surface-modified elastomeric substrate to provide (i.e., produce) a strained surface-modified elastomeric substrate, (iv) spraying (i.e., discharging, dispensing, etc.) a cell-containing composition onto the strained surface-modified elastomeric substrate to provide (i.e., produce) a disordered cell-containing microarray, and (v) relaxing the disordered cell-containing microarray to provide (i.e., produce) the ordered (e.g., patterned) cell-containing microarray.

In some embodiments, the method for preparing an ordered (e.g., patterned) cell-containing microarray comprises process (A). In other embodiments, the method for preparing an ordered (e.g., patterned) cell-containing microarray comprises process (B).

The method comprises providing an elastomeric substrate. The elastomeric substrate can be any suitable substrate comprising an elastomeric polymer material. For example, the elastomeric substrate can comprise a diene-based elastomeric polymer material (e.g., polyisoprene, polybutadiene, polychloroprene, etc), a non-diene-based elastomeric polymer material (e.g., butyl rubber, polysiloxane, polyurethane, and fluoro-based elastomers), a thermoplastic elastomeric polymer material (e.g., copolymers prepared from certain combinations of styrene, isoprene, and butadiene), or a combination thereof. In some embodiments, the elastomeric substrate comprises a non-diene-based elastomeric material (e.g., butyl rubber, polysiloxane, polyurethane, and fluoro-based elastomers). In certain embodiments, the elastomeric substrate comprises a silane-based material. Typically, the silane-based material is a polysiloxane (e.g., silicone) made up of one or more siloxanes having the general formula $—R_2Si—O—SiR_2—$, where R is an organic group (e.g., an alkyl group, a heteroalkyl group, an alkenyl group, a heteroalkenyl group, an alkynyl group, a heteroalkynyl group, a cycloalkyl group, a heterocycloalkyl group, an aryl group, a heteroaryl group, an arylalkyl group, a heteroarylalkyl group, or a combination thereof). In preferred embodiments, the elastomeric substrate comprises polydimethylsiloxane (PDMS) such as PDMS formulated using a commercial Sylgard 184 kit or the like.

Variable R can be any suitable substituent attached to a silicon atom present in the siloxane monomer. For example, each R independently is $C_{1-10}$ alkyl, $C_{2-10}$ alkenyl, $C_{2-10}$ alkynyl, $C_{2-10}$ heteroalkyl, $C_{2-10}$ heteroalkenyl, $C_{2-10}$ heteroalkynyl, $C_{3-10}$ cycloalkyl, $C_{3-10}$ heterocycyl, $C_{6-10}$ aryl, $C_{6-10}$ heteroaryl, $C_{6-10}$ arylalkyl, or $C_{6-10}$ heteroarylalkyl. In some embodiments, each R independently is $C_{1-10}$ alkyl, $C_{2-10}$ alkenyl, $C_{2-10}$ alkynyl, $C_{2-10}$ heteroalkyl, $C_{2-10}$ heteroalkenyl, or $C_{2-10}$ heteroalkynyl. In certain embodiments, each R independently is $C_{1-10}$ alkyl, e.g., methyl or ethyl.

The method comprises modifying a surface of the elastomeric substrate to provide (i.e., produce) a surface-modified elastomeric substrate. As used herein, the phrase "modifying a surface" refers to a process of treating a surface to change the chemical properties of the surface. In some embodiments, modifying the surface of the elastomeric substrate comprises masking the elastomeric substrate and chemically modifying at least a portion of the surface of the elastomeric substrate exposed by the masking or exposed through the masking to provide the surface-modified elastomeric substrate. In other words, modifying the surface of the elastomeric substrate comprises applying a mask to the elastomeric substrate and chemically modifying at least a portion of the surface of the elastomeric substrate exposed by the mask to provide the surface-modified elastomeric substrate. As a result of modifying a surface of the elastomeric substrate to provide (i.e., produce) a surface-modified elastomeric substrate, the surface-modified elastomeric substrate is chemically ordered (i.e., patterned) according to the masking pattern.

In general, the goal of modifying the surface of the elastomeric substrate is to (i) provide at least a portion of the surface of the elastomeric substrate that is hydrophilic, (ii) provide at least a portion of the surface of the elastomeric substrate that promotes cell adhesion, and/or (iii) provide at least a portion of the surface of the elastomeric substrate that is capable of attachment of a chemical moiety by chemically, thermally, and/or photolytically treating the surface-modified elastomeric substrate. Thus, in some embodiments, chemically modifying at least a portion of the surface of the elastomeric substrate provides at least a portion of the surface of the elastomeric substrate that is hydrophilic. Alternatively, or additionally, chemically modifying at least a portion of the surface of the elastomeric substrate provides at least a portion of the surface of the elastomeric substrate that enables assembly of disordered cell-containing microarray into ordered cell containing microarray by hydrophobicity contrast and promotes cell adhesion or is capable of attachment of a chemical moiety by chemically, thermally, and/or photolytically treating the surface-modified elastomeric substrate in the ordered cell-containing microarray.

In some embodiments, the method comprises chemically modifying at least a portion of the surface of the elastomeric substrate by oxidizing the surface. The surface of the elastomeric substrate can be oxidized by any suitable means. For example, oxidizing the surface of the elastomeric substrate can comprise treating the surface with ozone or plasma oxidation. Without wishing to be bound by any particular theory, it is believed that oxidizing the surface of the elastomeric substrate provides a hydrophilic surface for which cell culture media will be attracted to via hydrophilic interactions (e.g., Van der Waals forces) and/or promotes cell adhesion. Alternatively, or additionally, oxidizing the surface of the elastomeric substrate provides a synthetic handle for which further surface modifications can be made. For instance, in embodiments where the elastomeric substrate comprises PDMS, the PDMS can be oxidized with ozone or plasma oxidation to produce an ordered array (e.g., pattern) of hydroxylated PDMS. Without wishing to be bound by any particular theory, it is believed that the hydroxylated PDMS provides a differentiated surface that is hydrophilic compared to unmodified PDMS, and is capable of promoting cell adhesion relative to unmodified PDMS. In addition, the hydroxylated PDMS provides a synthetic handle for which further surface modifications can be made.

Alternatively, or in addition to oxidizing the elastomeric surface, chemically modifying at least a portion of the surface of the elastomeric substrate can comprise attaching to the surface of the elastomeric substrate a peptide-based adhesion promoter, a small molecule adhesion promoter (e.g., hyaluronic acid), a (meth)acrylate-containing compound, a (meth)acrylamide-containing compound, a polyethylene glycol-containing compound, a fluorocarbon (e.g., fluorinated alkyl, perfluorinated alkyl, etc.), a NHS-ester-containing compound, a maleimide-containing compound, an azide-containing compound, an alkyne-containing compound, or any combination thereof.

In some embodiments, chemically modifying at least a portion of the surface of the elastomeric substrate provides at least a portion of the surface of the elastomeric substrate that promotes cell adhesion. In certain embodiments, chemically modifying at least a portion of the surface of the elastomeric substrate comprises attaching to the surface of the elastomeric substrate a peptide-based adhesion promoter. The peptide-based adhesion promoter can be any suitable peptide capable of promoting adhesion of a cell to the surface. For example, the peptide-based adhesion promoter can be Arg-Gly-Asp (RGD), polylysine, polyarginine, polyhistidine, fibronectin, laminin (e.g., laminin-111), collagen (e.g., collagen IV), or a combination thereof. In certain embodiments, the peptide-based adhesion promoter is polylysine (e.g., poly-L-lysine). In other embodiments, chemically modifying at least a portion of the surface of the elastomeric substrate comprises attaching to the surface of the elastomeric substrate a small molecule adhesion promoter (e.g., hyaluronic acid).

In some embodiments, chemically modifying at least a portion of the surface of the elastomeric substrate provides at least a portion of the surface of the elastomeric substrate that is capable of attachment of a chemical moiety by chemically, thermally, and/or photolytically treating the surface-modified elastomeric substrate in the ordered cell-containing microarray. In other words, the surface of the elastomeric substrate can be chemically modified with a reactive (e.g., chemically, thermally, and/or photolytically) chemical moiety that can be used to further modify the surface (e.g., to attach the cell-containing composition to the surface-modified elastomeric substrate). For example, at least a portion of the surface of the elastomeric substrate can be modified with a (meth)acrylate-containing compound, a (meth)acrylamide-containing compound, a polyethylene glycol-containing compound, a NHS-ester-containing compound, a maleimide-containing compound, an azide-containing compound, an alkyne-containing compound, or any combination thereof. In certain embodiments, at least a portion of the surface of the elastomeric substrate is modified with a (meth)acrylate-containing compound.

In some embodiments, chemically modifying at least a portion of the surface of the elastomeric substrate provides at least a portion of the surface of the elastomeric substrate that is capable of increasing the wettability contrast between the pattern zone and the field. For example, chemically modifying at least a portion of the surface of the elastomeric substrate can provide at least a portion of the surface with increased hydrophobicity. In some embodiments, at least a portion of the surface of the elastomeric substrate can be modified with a fluorocarbon (e.g., fluorinated alkyl, perfluorinated alkyl, etc.).

The method comprises spraying (i.e., discharging, dispensing, etc.) a cell-containing composition onto the surface-modified elastomeric substrate or the strained surface-modified elastomeric substrate to provide a disordered cell-containing microarray. The cell-containing composition can be sprayed (i.e., discharged, dispensed, etc.) by any suitable means. Generally, spraying the cell-containing composition generates droplets, which are readily dispersed on the surface-modified elastomeric substrate. The droplets can be generated by any suitable system. For example, the droplets can be generated by controlled mixing of an aqueous solution (e.g., a buffer, a cell suspension media, or a cell culture media) and a pressurized gas (e.g., air or nitrogen), which exit the system (e.g., spraying nozzle or a syringe) at a desired pressure and flow rate. See FIG. 1 for an exemplary nozzle design.

The cell-containing composition can be sprayed (i.e., discharged, dispensed, etc.) at any suitable pressure as long as the desired droplet size and cell viability level is achieved. For example, the cell-containing composition can be sprayed (i.e., discharged, dispensed, etc.) at a pressure of about 5 kPa or more, a pressure of about 10 kPa or more, a pressure of about 15 kPa or more, a pressure of about 20 kPa or more, a pressure of about 25 kPa or more, a pressure of about 30 kPa or more, a pressure of about 35 kPa or more, or a pressure of about 40 kPa or more. Alternatively, or additionally, the cell-containing composition can be sprayed (i.e., discharged, dispensed, etc.) at a pressure of about 100 kPa or less, a pressure of about 95 kPa or less, a pressure of about 90 kPa or less, a pressure of about 85 kPa or less, a pressure of about 80 kPa or less, a pressure of about 75 kPa or less, a pressure of about 70 kPa or less, a pressure of about 65 kPa or less, or a pressure of about 60 kPa or less. Thus, the cell-containing composition can be sprayed (i.e., discharged, dispensed, etc.) at a pressure bounded by any two of the aforementioned endpoints. For example, the cell-containing composition can be sprayed (i.e., discharged, dispensed, etc.) at a pressure of about 5 kPa to about 100 kPa, of about 10 kPa to about 100 kPa, of about 20 kPa to about 100 kPa, of about 30 kPa to about 100 kPa, of about 40 kPa to about 100 kPa, of about 5 kPa to about 90 kPa, of about 10 kPa to about 90 kPa, of about 20 kPa to about 90 kPa, of about 30 kPa to about 90 kPa, of about 40 kPa to about 90 kPa, of about 5 kPa to about 80 kPa, of about 10 kPa to about 80 kPa, of about 20 kPa to about 80 kPa, of about 30 kPa to about 80 kPa, of about 40 kPa to about 80 kPa, of about 5 kPa to about 70 kPa, of about 10 kPa to about 70 kPa, of about 20 kPa to about 70 kPa, of about 30 kPa to about 70 kPa, of about 40 kPa to about 70 kPa, of about 5 kPa to about 60 kPa, of about 10 kPa to about 60 kPa, of about 20 kPa to about 60 kPa, of about 30 kPa to about 60 kPa, or of about 40 kPa to about 60 kPa. In some embodiments, the cell-containing composition is sprayed at a pressure of about 5 kPa to about 100 kPa. In certain embodiments, the cell-containing composition is sprayed at a pressure of about 30 kPa to about 60 kPa.

Without wishing to be bound by any particular theory, it is believed that as the pressure is increased, the average size for the total droplet population decreases, eventually reducing to a size that is incapable of containing cells. Alternatively, it is believed that as the pressure is decreased, the average size for the total droplet population increases, eventually increasing to a size that is capable of containing more than one (e.g., more than two, more than three, etc.). In addition, increasing the pressure at which the cell-containing composition is sprayed (i.e., discharged, dispensed, etc.) can have a significant effect on cell damage as a result of sheer stress.

The cell-containing composition can be sprayed (i.e., discharged, dispensed, etc.) at any suitable flow rate as long as the desired droplet size and cell viability level is achieved. For example, the cell-containing composition can be sprayed (i.e., discharged, dispensed, etc.) at a flow rate of about 5 $\mu Lmin^{-1}$ or more, a flow rate of about 10 $\mu Lmin^{-1}$ or more, a flow rate of about 15 $\mu Lmin^{-1}$ or more, a flow rate of about 20 $\mu Lmin^{-1}$ or more, a flow rate of about 25 $\mu Lmin^{-1}$ or more, a flow rate of about 30 $\mu Lmin^{-1}$ or more, a flow rate of about 35 $\mu Lmin^{-1}$ or more, or a flow rate of about 40 $\mu Lmin^{-1}$ or more. Alternatively, or additionally, the cell-containing composition can be sprayed (i.e., discharged, dispensed, etc.) at a flow rate of about 100 $\mu Lmin^{-1}$ or less, a flow rate of about 95 $\mu Lmin^{-1}$ or less, a flow rate of about 90 $\mu Lmin^{-1}$ or less, a flow rate of about 85 $\mu Lmin^{-1}$ or less, a flow rate of about 80 $\mu Lmin^{-1}$ or less, a flow rate of about 75 $\mu Lmin^{-1}$ or less, a flow rate of about 70 $\mu Lmin^{-1}$ or less, a flow rate of about 65 $\mu Lmin^{-1}$ or less, or a flow rate of about 60 $\mu Lmin^{-1}$ or less. Thus, the cell-containing composition can be sprayed (i.e., discharged, dispensed, etc.) at a flow rate bounded by any two of the aforementioned endpoints. For example, the cell-containing composition can be sprayed (i.e., discharged, dispensed, etc.) at a flow rate of about 5 $\mu Lmin^{-1}$ to about 100 $\mu Lmin^{-1}$, of about 10 $\mu Lmin^{-1}$ to about 100 $\mu Lmin^{-1}$, of about 20 $\mu Lmin^{-1}$ to about 100 $\mu Lmin^{-1}$, of about 30 $\mu Lmin^{-1}$ to about 100 $\mu Lmin^{-1}$, of about 40 $\mu Lmin^{-1}$ to about 100 $\mu Lmin^{-1}$, of about 5 $\mu Lmin^{-1}$ to about 90 $\mu Lmin^{-1}$, of about 10 $\mu Lmin^{-1}$ to about 90 $\mu Lmin^{-1}$, of about 20 $\mu Lmin^{-1}$ to about 90 $\mu Lmin^{-1}$, of about 30 $\mu Lmin^{-1}$ to about 90 $\mu Lmin^{-1}$, of about 40 $\mu Lmin^{-1}$ to about 90 $\mu Lmin^{-1}$, of about 5 $\mu Lmin^{-1}$ to about 80 $\mu Lmin^{-1}$, of about 10 $\mu Lmin^{-1}$ to about 80 $\mu Lmin^{-1}$, of about 20 $\mu Lmin^{-1}$ to about 80 $\mu Lmin^{-1}$, of about 30 $\mu Lmin^{-1}$ to about 80 $\mu Lmin^{-1}$, of about 40 $\mu Lmin^{-1}$ to about 80 $\mu Lmin^{-1}$, of about 5 $\mu Lmin^{-1}$ to about 70 $\mu Lmin^{-1}$, of about 10 $\mu Lmin^{-1}$ to about 70 $\mu Lmin^{-1}$, of about 20 $\mu Lmin^{-1}$ to about 70 v, of about 30 $\mu Lmin^{-1}$ to about 70 $\mu Lmin^{-1}$, of about 40 $\mu Lmin^{-1}$ to about 70 $\mu Lmin^{-1}$, of about 5 $\mu Lmin^{-1}$ to about 60 $\mu Lmin^{-1}$, of about 10 $\mu Lmin^{-1}$ to about 60 $\mu Lmin^{-1}$, of about 20 $\mu Lmin^{-1}$ to about 60 $\mu Lmin^{-1}$, of about 30 $\mu Lmin^{-1}$ to about 60 $\mu Lmin^{-1}$, or of about 40 $\mu Lmin^{-1}$ to about 60 $\mu Lmin^{-1}$. In some embodiments, the cell-containing composition is sprayed at a flow rate of about 10 $\mu Lmin^{-1}$ to 100 $\mu Lmin^{-1}$. In certain embodiments, the cell-containing composition is sprayed at a flow rate of about 40 $\mu Lmin^{-1}$ to 80 $\mu Lmin^{-1}$.

The cell-containing composition can be sprayed (i.e., discharged, dispensed, etc.) at any suitable distance from the surface-modified elastomeric substrate or the strained surface-modified elastomeric substrate as long as the desired droplet size and cell viability level is achieved. For example, the cell-containing composition can be sprayed (i.e., discharged, dispensed, etc.) at a distance of about 1 cm or more, a distance of about 5 cm or more, a distance of about 10 cm or more, a distance of about 15 cm or more, or a distance of about 20 cm or more. Alternatively, or additionally, the cell-containing composition can be sprayed (i.e., discharged, dispensed, etc.) at a distance of about 100 cm or less, a distance of about 90 cm or less, a distance of about 80 cm or less, a distance of about 70 cm or less, a distance of about 60 cm or less, a distance of about 50 cm or less, a distance of about 40 cm or less, a distance of about 30 cm or less, a distance of about 20 cm or less, a distance of about 15 cm or less, or a distance of about 10 cm or less. Thus, the cell-containing composition can be sprayed (i.e., discharged, dispensed, etc.) at a distance bounded by any two of the aforementioned endpoints. For example, the cell-containing composition can be sprayed (i.e., discharged, dispensed, etc.) at a distance of about 1 cm to about 100 cm, of about 5 cm to about 100 cm, of about 10 cm to about 100 cm, of about 15 cm to about 100 cm, of about 20 cm to about 100 cm, of about 1 cm to about 50 cm, of about 5 cm to about 50 cm, of about 10 cm to about 50 cm, of about 15 cm to about 50 cm, of about 20 cm to about 50 cm, of about 1 cm to about 20 cm, of about 5 cm to about 20 cm, of about 10 cm to about 20 cm, of about 1 cm to about 15 cm, or of about 5 cm to about 15 cm. In some embodiments, the cell-containing composition is sprayed at a distance of about 1 cm to about 20 cm from the surface-modified elastomeric substrate or the strained surface-modified elastomeric substrate. In certain embodiments, the cell-containing composition is sprayed at a distance of about 5 cm to about 15 cm from the surface-modified elastomeric substrate or the strained surface-modified elastomeric substrate.

Spraying (i.e., discharging, dispensing, etc.) the cell-containing composition can produce droplets of the cell-containing composition with any suitable average particle diameter. For example, spraying the cell-containing composition can produce droplets of the cell-containing composition with an average particle diameter of at least about 10 μm, an average particle diameter of at least about 20 μm, an average particle diameter of at least about 30 μm, an average particle diameter of at least about 40 μm, or an average particle diameter of at least about 50 μm. Alternatively, or additionally, spraying the cell-containing composition can produce droplets of the cell-containing composition with an average particle diameter of 200 μm or less, an average particle diameter of 150 μm or less, an average particle diameter of 100 μm or less, an average particle diameter of 90 μm or less, or an average particle diameter of 80 μm or less. Thus, spraying the cell-containing composition can produce droplets of the cell-containing composition with an average particle diameter bounded by any two of the aforementioned endpoints. For example, spraying the cell-containing composition can produce droplets of the cell-containing composition with an average particle diameter of about 10 μm to about 200 μm, of about 10 μm to about 150 μm, of about 10 μm to about 100 μm, of about 10 μm to about 90 μm, of about 10 μm to about 80 μm, of about 20 μm to about 200 μm, of about 20 μm to about 150 μm, of about 20 μm to about 100 μm, of about 20 μm to about 90 μm, of about 20 μm to about 80 μm, of about 30 μm to about 200 μm, of about 30 μm to about 150 μm, of about 30 μm to about 100 μm, of about 30 μm to about 90 μm, of about 30 μm to about 80 μm, of about 40 μm to about 200 μm, of about 40 μm to about 150 μm, of about 40 μm to about 100 μm, of about 40 μm to about 90 μm, of about 40 μm to about 80 μm, of about 50 μm to about 200 μm, of about 50 μm to about 150 μm, of about 50 μm to about 100 μm, of about 50 μm to about 90 μm, or of about 50 μm to about 80 μm. In some embodiments, spraying the cell-containing composition can produce droplets of the cell-containing composition with an average particle diameter of about 30 μm to about 200 μm. In certain embodiments, spraying the cell-containing composition can produce droplets of the cell-containing composition with an average particle diameter of about 40 μm to about 100 μm.

Generally, spraying (i.e., discharging, dispensing, etc.) the cell-containing composition onto the surface-modified elastomeric substrate or the strained surface-modified elastomeric substrate provides (i.e., produces) a cell viability on the surface-modified elastomeric substrate or the strained surface-modified elastomeric substrate of at least about 50%. In some embodiments, spraying (i.e., discharging, dispensing, etc.) the cell-containing composition onto the surface-modified elastomeric substrate or the strained surface-modified elastomeric substrate provides (i.e., produces) a cell viability on the surface-modified elastomeric substrate or the strained surface-modified elastomeric substrate of at least about 60%, at least about 70%, at least about 80%, or at least about 90%.

The cell-containing composition can comprise any suitable cell culture. For example, the cell-containing composition can comprise animal cell culture, plant tissue culture, fungal culture, microbiological culture, tissue culture, organ culture, viral culture, or a combination thereof. In some embodiments, the cell-containing composition comprises animal cell culture, plant tissue culture, tissue culture, organ culture, or a combination thereof. In certain embodiments, the cell-containing composition comprises plant-derived cell culture or animal-derived cell culture, and preferably animal-derived cell culture. The cell-containing composition can comprise cells established as cultured cells or primary cells obtained from biological tissues. For example, the cell-containing composition can comprise differentiated or undifferentiated somatic cells (e.g., healthy or cancerous), stem cells (e.g., induced pluripotent stem cells (iPSCs)), or a combination thereof. In certain embodiments, the cell-containing composition comprises pluripotent stem cells, which include embryonic stem cells, induced pluripotent stem cells, mesenchymal stem cells, neural stem cells, or a combination thereof. The cells can be differentiated cells such as, for example, kidney cells, nerve cells, gastrointestinal (e.g., human colon carcinoma cells such as HCT116), corneal endothelial cells, hepatocytes, fibroblasts, pancreatic islet cells, chondrocytes, or myocardial cells. Alternatively, or additionally, the cells can be induced to differentiate from umbilical cord blood, bone marrow, fat, blood-derived tissue stem cells, tumorigenic cells, cells transformed by genetic engineering techniques, or cells infected with viral vectors. In some embodiments, the cells are labelled for analysis purposes.

The cell-containing composition can comprise any suitable component other than the cells, particularly those necessary for sustaining cell viability. In some embodiments, the cell-containing composition comprises a liquid media. The liquid media can contain any suitable components as long as the liquid media sustains cell viability and is capable of being sprayed (i.e., discharged, dispensed, etc.). For example, the liquid media can comprise a buffer, a suspension media, a culture media), or a combination thereof. In some embodiments, the cell-containing composition comprises a gel media or a gel media precursor. In certain embodiments, the gel media or gel media precursor comprises a hydrogel or a hydrogel precursor (e.g., Matrigel™ Matrix or Matrigel™ Matrix precursor).

Figure 29:
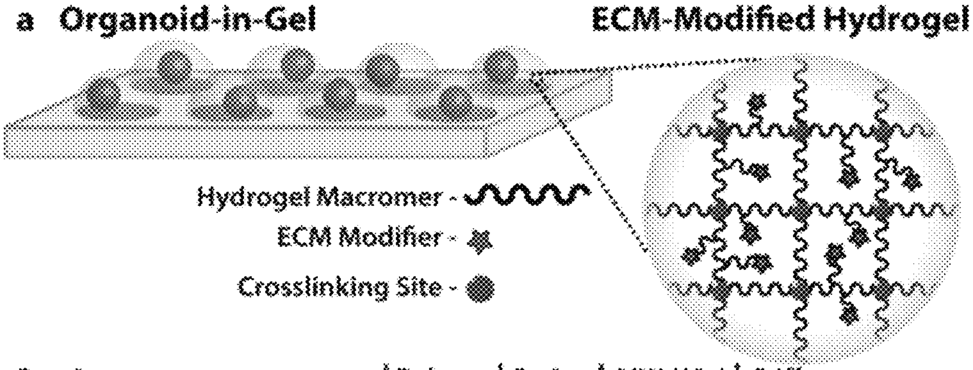
FIG. 29 is a schematic showing exemplary components for preparing an extracellular matrices-modified hydrogel network for use in the preparation of a microassembly of organoids-in-gels. Provided is an illustration of a mechanically/chemically tuned PEG hydrogel (a), where the stiffness and chemistry of the scaffold are readily modified using different macromers (b-c) and matrix modifiers with thiol/amine reactive conjugation sites (d-e). The stiffness can also be controlled using select molecular weights and crosslinker densities.
Figure 29:
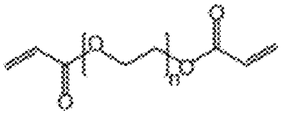
Figure 29:
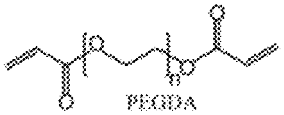
Figure 29:
Figure 29:
Figure 29:
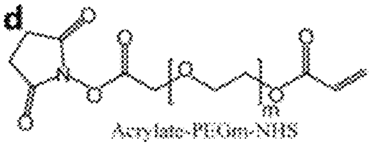
Figure 29:
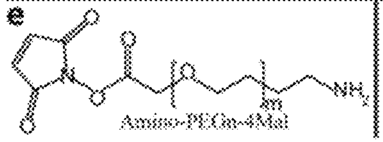

In some embodiments, the gel matrix is synthetically prepared according to the structure shown in FIG. 29(*a*). In particular, the gel matrix can be prepared from a gel matrix precursor comprising one or more hydrogel macromer, one or more extracellular matrix modifier, one or more cross-linking site, or combinations thereof. The structure, integrity, and physical properties of the gel matrix can be controlled by modifying the concentrations of the gel matrix precursor components, the structures (e.g., number of PEG units or molecular weight) of the gel matrix precursor components, or the degree of curing. The gel matrix can be formed by photochemically curing the gel matrix precursor components or chemically curing the gel matrix precursor components.

In some embodiments, the gel matrix is prepared from a gel matrix precursor comprising one or more compounds seleced from the Formula I-IV or a combination thereof:

Formula I

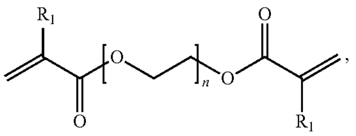

Formula II

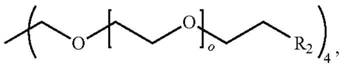

-continued

Formula III

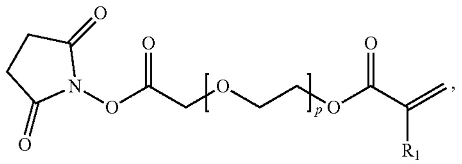

and

Formula IV

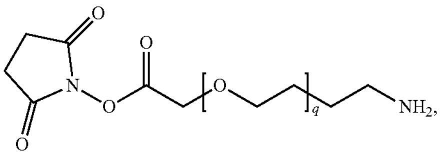

wherein each $R_1$ independently is an alkyl group, each of variables n, o, p, and q independently is and integer from about 1 to about 200 (e.g., from about 1 to about 100, from about 1 to about 50, from about 1 to about 20, from about 2 to about 200, from about 2 to about 100, from about 2 to about 50, or from about 2 to about 20), and each $R_2$ independently is (meth)acrylate, (meth)acrylamide, SH, or $NH_2$. In some embodiments, each $R_1$ independently is methyl or hydrogen. In certain embodiments, each $R_1$ is hydrogen.

Spraying (i.e., discharging, dispensing, etc.) the cell-containing composition onto the surface-modified elastomeric substrate or the strained surface-modified elastomeric substrate provides a disordered cell-containing microarray. In order to convert the disordered cell-containing microarray to an ordered (e.g., patterned) cell-containing microarray, a strain needs to be applied to the elastomeric substrate or the strain needs to be released (e.g., relaxed) from the strained elastomeric substrate. Thus, the method comprises applying a strain to the disordered cell-containing microarray to provide the ordered (e.g., patterned) cell-containing microarray or relaxing the disordered cell-containing microarray to provide the ordered cell-containing microarray.

Figure 14:
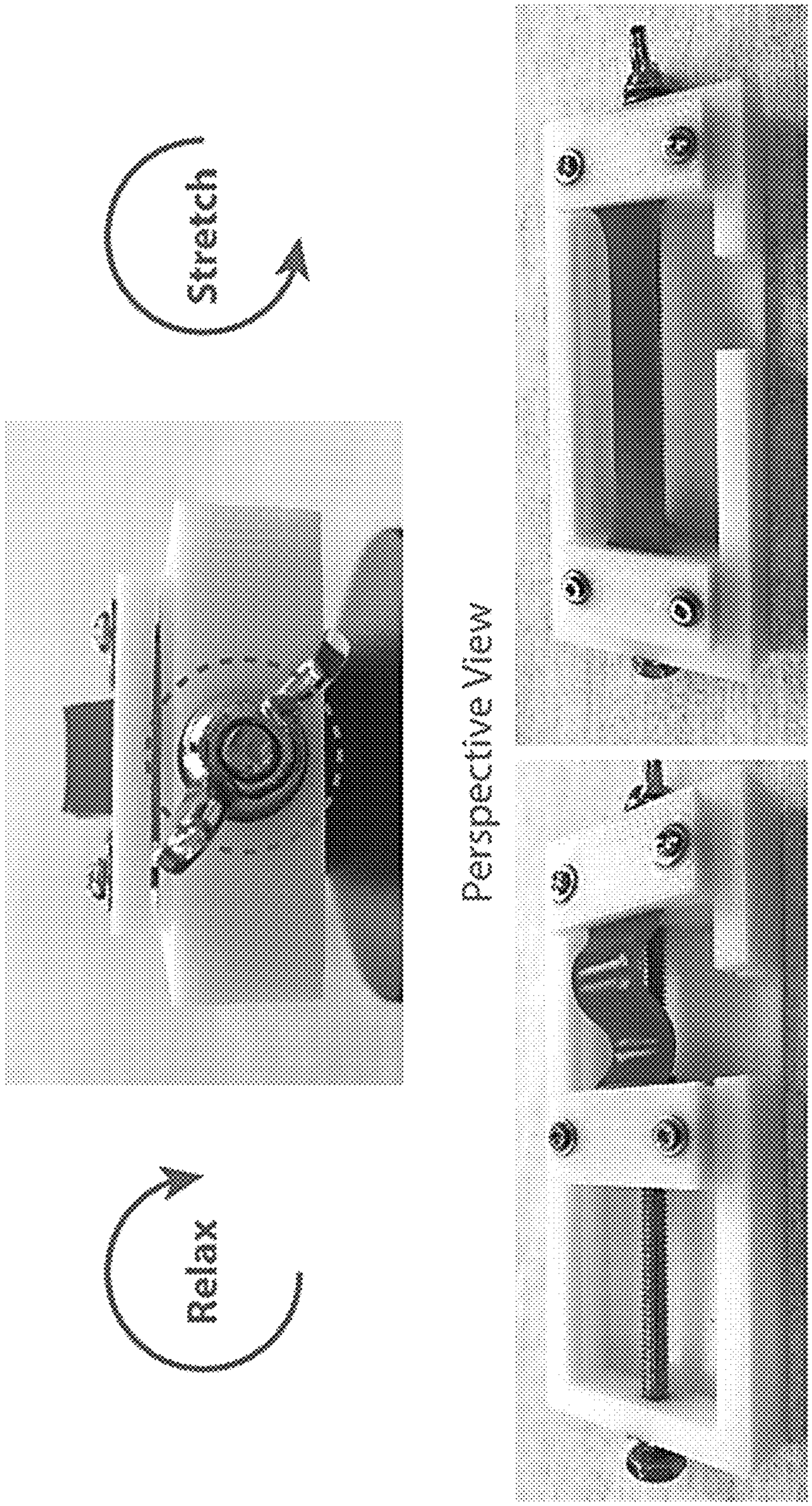
FIG. 14 shows an exemplary stretcher device for elastomeric materials made by 3D-printing.

Without wishing to be bound to any particular theory, it is believed that applying a strain to the disordered cell-containing microarray or releasing (e.g., relaxing) the strain of the disordered cell-containing microarray induces the droplets to organize based on hydrophobic/hydrophilic interactions and/or cell adhesion effects. The strain can be applied and/or released (e.g., relaxed) by any suitable means. For example, the elastomeric substrate can be twisted, stretched, bent (e.g., folded), compressed, any combination thereof, or any inverse thereof. In some embodiments, applying the strain to the disordered cell-containing microarray or the surface-modified elastomeric substrate comprises stretching the elastomeric substrate. The elastomeric substrate can be stretched in any suitable direction and any suitable distance. For example, the elastomeric substrate can be stretched uniaxially, biaxially, or omnidirectionally (i.e., in all directions). In certain embodiments, the elastomeric substrate is stretched uniaxially or biaxially. FIG. 14 provides an image of an exemplary device for stretching the elastomeric substrate.

In some embodiments, the method further comprises relaxing the elastomeric substrate after applying a strain to the disordered cell-containing microarray to provide the ordered (e.g., patterned) cell-containing microarray. In other words, the elastomeric substrate can be returned to its resting state after the strain is applied.

In some embodiments, the method further comprises attaching the cell-containing composition to the surface-modified elastomeric substrate in the ordered cell-containing microarray by chemically, thermally, and/or photolytically treating the surface-modified elastomeric substrate in the ordered cell-containing microarray. In other words, the cell-containing composition comprising a liquid media (e.g., a gel media or a gel media precursor) can be attached to the surface by forming a chemical bond (e.g., covalent or ionic) so as to form a three-dimensional microarray. Thus, in a second aspect, a method for preparing an ordered cell-containing microarray includes process (A) or process (B):

(A) (i) providing an elastomeric substrate,
- (ii) modifying a surface of the elastomeric substrate to provide (i.e., produce) a surface-modified elastomeric substrate,
- (iii) spraying (i.e., discharging, dispensing, etc.) a cell-containing composition onto the surface-modified elastomeric substrate to provide (i.e., produce) a disordered cell-containing microarray,
- (iv) applying a strain to the disordered cell-containing microarray to provide (i.e., produce) the ordered (e.g., patterned) cell-containing microarray, and
- (v) attaching the cell-containing composition to the surface-modified elastomeric substrate in the ordered (e.g., patterned) cell-containing microarray by chemically, thermally, and/or photolytically treating the surface-modified elastomeric substrate in the ordered (e.g., patterned) cell-containing microarray;

(B) (i) providing an elastomeric substrate,
- (ii) modifying a surface of the elastomeric substrate to provide (i.e., produce) a surface-modified elastomeric substrate,
- (iii) applying a strain to the surface-modified elastomeric substrate to provide (i.e., produce) a strained surface-modified elastomeric substrate,
- (iv) spraying (i.e., discharging, dispensing, etc.) a cell-containing composition onto the strained surface-modified elastomeric substrate to provide (i.e., produce) a disordered cell-containing microarray,
- (v) relaxing the disordered cell-containing microarray to provide (i.e., produce) the ordered (e.g., patterned) cell-containing microarray, and
- (vi) attaching the cell-containing composition to the surface-modified elastomeric substrate in the ordered (e.g., patterned) cell-containing microarray by chemically, thermally, and/or photolytically treating the surface-modified elastomeric substrate in the ordered (e.g., patterned) cell-containing microarray.

The cell-containing composition can be attached by chemically, thermally, and/or photolytically treating the surface-modified (i.e., modified with a (meth)acrylate-containing compound, a (meth)acrylamide-containing compound, a polyethylene glycol-containing compound, a fluorocarbon (e.g., fluorinated alkyl, perfluorinated alkyl, etc.), a NHS-ester-containing compound, a maleimide-containing compound, an azide-containing compound, an alkyne-containing compound, or any combination thereof) elastomeric substrate. Chemically, thermally, and/or photolytically treating the surface-modified elastomeric substrate can form a chemical bond (e.g., covalent or ionic) by any suitable means. For example, a chemical bond can be formed by a substitution reaction, a condensation reaction, an addition reaction, a click reaction, a radical reaction, a metathesis reaction, a cyclization reaction, or a combination thereof. In certain embodiments, the cell-containing composition is attached to the surface-modified elastomeric substrate in the ordered cell-containing microarray by photolytically treating the surface-modified elastomeric substrate in the ordered cell-containing microarray. For example, the surface of the elastomeric substrate can be modified with a (meth)acrylate-containing compound or a (meth)acrylamide-containing compound, which can form a chemical bond through photo-induced radical chemistry with a (meth)acrylate-containing compound or a (meth)acrylamide-containing compound present in the cell-containing composition.

In some embodiments, the method further comprises transferring the ordered cell-containing microarray to a cell culture media to induce and/or sustain growth of a cell. The cell culture media can be any suitable media capable of inducing and/or sustaining growth of a cell. In certain embodiments, the cell culture media further comprises an agent to induce differentiation of a cell.

In some embodiments, the ordered cell-containing microarray is a two-dimensional microarray. In other words, the cells of the cell-containing composition adhere to the surface based on hydrophilic and/or chemical interactions with chemical moieties that promote cell adhesion. The unique combination of cell-containing droplets and two-dimensional surface patterns in micro-assembly of cells-in-droplets (μACD) provides opportunities for a wide spectrum of biological applications. For example, the two-dimensional array can be used for drug screening and analytical assays right after droplets are assembled and cells in the assembled droplets are in suspended states. Moreover, the two-dimensional array enables tissue engineering and mechanobiology studies where cells are attached to the substrate and proliferate. In addition to these monoculture applications, the micro-assembly of cells-in-droplets (μACD) described herein can be expanded to co-culture of multiple cells.

In other embodiments, the ordered cell-containing microarray is a three-dimensional microarray. In other words, the cells of the cell-containing composition are maintained in a cell-containing composition (e.g., a gel media) that has been attached to the surface-modified elastomeric substrate in the ordered cell-containing microarray by chemically, thermally, and/or photolytically treating the surface-modified elastomeric substrate in the ordered cell-containing microarray. The three-dimensional microarray allows for preparation of micro-assembled organoids-in-gels (mAOG). The micro-assembled organoids-in-gels (mAOG) can be used for organoid-based cancer models. Since the organoids are self-renewing and self-organizing three-dimensional (3D) clusters of cells, they can easily mimic the functionality of macroscale tissues.

Without wishing to be bound by any particular theory, the characteristics of organoids make them ideal candidates for next-generation tumor models that recapitulate the inherent inter-/intra-patient heterogeneities associated with tumorigenesis and metastasis. For instance, this promise can be exemplified by exposing the same drug compounds to healthy and tumor organoids from the same patients for personalized drug screening. However, organoid heterogeneity derived from the disorderly growth/assembly of cells limits their wide-spread adoption as cancer models, in which meaningful biological observations can be made only when one can create thousands of nearly identical organoids within defined, uniform microenvironments. Specifically, the limitations associated with organoid models are the inherent biological diversity of organoids and the mechanical and chemical diversity required of the cellular scaffolds. Organoid biodiversity manifests naturally from the range of three-dimensional cellular architectures and phenotypic identities that arise during organoid development. To preserve this characteristic requires large populations of organoids to be surveyed for meaningful conclusions. The limited chemical/mechanical diversity of cellular scaffold materials minimizes the range of organoid types accessible, as the mechanics and chemistry of the scaffolds are critical to the cellular aggregation and assembly process. Therefore, to fully realize the potential of organoid as next generation cancer models, the generation of large batches of organoids in a parallel fashion in controlled and desired cellular scaffolds is necessary. The three-dimensional microarray described herein enables this approach.

System for Preparing an Ordered Cell-Containing Microarray

The invention further provides a system for preparing an ordered cell-containing microarray, including all features thereof, described herein. Thus, in a third aspect, the invention provides a system for preparing an ordered (e.g., patterned) cell-containing microarray comprising a means for spraying (i.e., discharging, dispensing, etc.) a cell-containing composition and a means for mechanically straining an elastomeric substrate.

The system comprises a means for spraying (i.e., discharging, dispensing, etc.) a cell-containing composition. The means for spraying (i.e., discharging, dispensing, etc.) can comprise any combination of inlets, outlets, compartments, hoses, nozzles, syringe, syringe pump, etc. necessary to spray (i.e., discharge, dispense, etc.) the cell-containing composition onto the surface-modified elastomeric substrate. In some embodiments, the means for spraying a cell-containing composition comprises an inlet for receiving a cell-containing composition, an inlet for receiving a pressurized gas (e.g., air or nitrogen gas), and an outlet for spraying (i.e., discharging, dispensing, etc.) droplets (e.g., microdroplets) comprising the cell-containing composition. The cell-containing composition can be received via an inlet from a compartment which holds the cell-containing composition. Similarly, the pressurized gas (e.g., air or nitrogen gas) can be received via an inlet from a compartment which holds the pressurized gas (e.g., air or nitrogen gas). In certain embodiments, the inlet for receiving a cell-containing composition, the inlet for receiving a pressurized gas (e.g., air or nitrogen gas), and the outlet for spraying (i.e., discharging, dispensing, etc.) droplets (e.g., microdroplets) comprising the cell-containing composition are connected via a T-joint (i.e., T-junction). See FIG. 1 for an exemplary design of the inlet for receiving a cell-containing composition, the inlet for receiving a pressurized gas (e.g., air or nitrogen gas), and the outlet for spraying (i.e., discharging, dispensing, etc.) droplets (e.g., microdroplets) comprising the cell-containing composition.

The outlet for spraying (i.e., discharging, dispensing, etc.) droplets (e.g., microdroplets) comprising the cell-containing composition can be any suitable outlet or nozzle as long as the desired droplet size and cell viability level is achieved. For example, the outlet or nozzle can be a coaxial nozzle (e.g., a coaxial pneumatic micro-nozzle) or the like.

The system comprises a means for mechanically straining an elastomeric substrate. The means for mechanically straining an elastomeric substrate can strain the elastomeric substrate by any suitable technique. For example, the strain can be applied to the elastomeric substrate by twisting, stretching, bending (e.g., folding), compressing, or any combination thereof. In some embodiments, the means for mechanically straining an elastomeric substrate stretches the elastomeric substrate. The elastomeric substrate can be stretched in any suitable direction and any suitable distance. For example, the elastomeric substrate can be stretched uniaxially, biaxially, or omnidirectionally (i.e., in all directions). In certain embodiments, the elastomeric substrate is stretched uniaxially or biaxially. See FIG. 14 for an exemplary design of the means for mechanically straining an elastomeric substrate.

The means for spraying (i.e., discharging, dispensing, etc.) a cell-containing composition can be positioned in any orientation with respect to the means for mechanically straining an elastomeric substrate as long as the means for spraying (i.e., discharging, dispensing, etc.) a cell-containing composition is capable of delivering the cell-containing composition to the surface-modified elastomeric substrate. In some embodiments, the means for spraying a cell-containing composition is movably positioned above the means for mechanically straining an elastomeric substrate.

The outlet for spraying droplets (e.g., microdroplets) comprising the cell-containing composition can be positioned any distance from (e.g., above) the means for mechanically straining an elastomeric substrate as long as the desired droplet size and cell viability level is achieved. For example, the outlet for spraying droplets (e.g., microdroplets) comprising the cell-containing composition can be positioned about 1 cm or more, about 5 cm or more, about 10 cm or more, about 15 cm or more, or about 20 cm or more from (e.g., above) the means for mechanically straining an elastomeric substrate. Alternatively, or additionally, the outlet for spraying droplets (e.g., microdroplets) comprising the cell-containing composition can be positioned about 100 cm or less, about 90 cm or less, about 80 cm or less, about 70 cm or less, about 60 cm or less, about 50 cm or less, about 40 cm or less, about 30 cm or less, about 20 cm or less, about 15 cm or less, or about 10 cm or less from (e.g., above) the means for mechanically straining an elastomeric substrate. Thus, the outlet for spraying droplets (e.g., microdroplets) comprising the cell-containing composition can be positioned at a distance from (e.g., above) the means for mechanically straining an elastomeric substrate bounded by any two of the aforementioned endpoints. For example, the outlet for spraying droplets (e.g., microdroplets) comprising the cell-containing composition can be positioned about 1 cm to about 100 cm, about 5 cm to about 100 cm, about 10 cm to about 100 cm, about 15 cm to about 100 cm, about 20 cm to about 100 cm, about 1 cm to about 50 cm, about 5 cm to about 50 cm, about 10 cm to about 50 cm, about 15 cm to about 50 cm, about 20 cm to about 50 cm, about 1 cm to about 20 cm, about 5 cm to about 20 cm, about 10 cm to about 20 cm, about 1 cm to about 15 cm, or about 5 cm to about 15 cm from (e.g., above) the means for mechanically straining an elastomeric substrate. In some embodiments, the outlet for spraying droplets (e.g., microdroplets) comprising the cell-containing composition is movably positioned about 1 cm to about 20 cm above the means for mechanically straining an elastomeric substrate. In certain embodiments, the outlet for spraying microdroplets comprising the cell-containing composition is movably positioned about 5 cm to about 15 cm above the means for mechanically straining an elastomeric substrate.

In some embodiments, the system for preparing an ordered cell-containing microarray further comprises a light source. Thus, in a fourth aspect, the invention provides a system for preparing an ordered (e.g., patterned) cell-containing microarray comprising a means for spraying a cell-containing composition, a means for mechanically straining an elastomeric substrate, and a light source.

The light source can be any suitable light source capable of initiating photo-induced radical chemistry to aid in attachment of a chemical moiety by photolytically treating the surface-modified elastomeric substrate. For example, the light source can be ultraviolet (UV) light.

The light source can be positioned in any orientation with respect to the means for mechanically straining an elastomeric substrate as long as the light source is capable of initiating photo-induced radical chemistry to aid in attachment of a chemical moiety by photolytically treating the surface-modified elastomeric substrate. In some embodiments, the light source is movably positioned below the means for mechanically straining an elastomeric substrate.

Figure 31B:
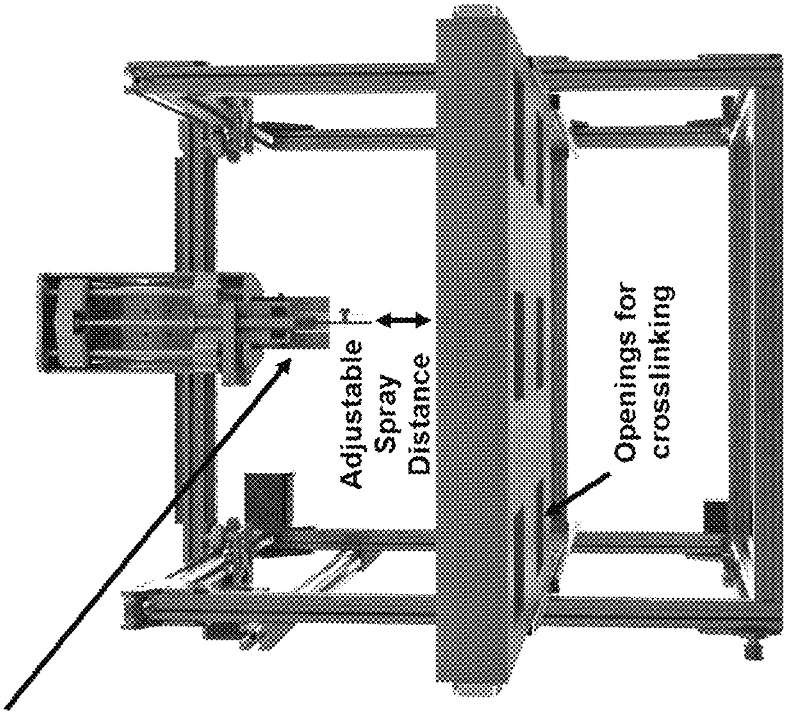
FIGS. 31A and 31B show an exemplary system for preparing an ordered (e.g., patterned) cell-containing microarray with FIG. 31A providing an aerial view and FIG. 31B providing a side view.
Figure 31A:
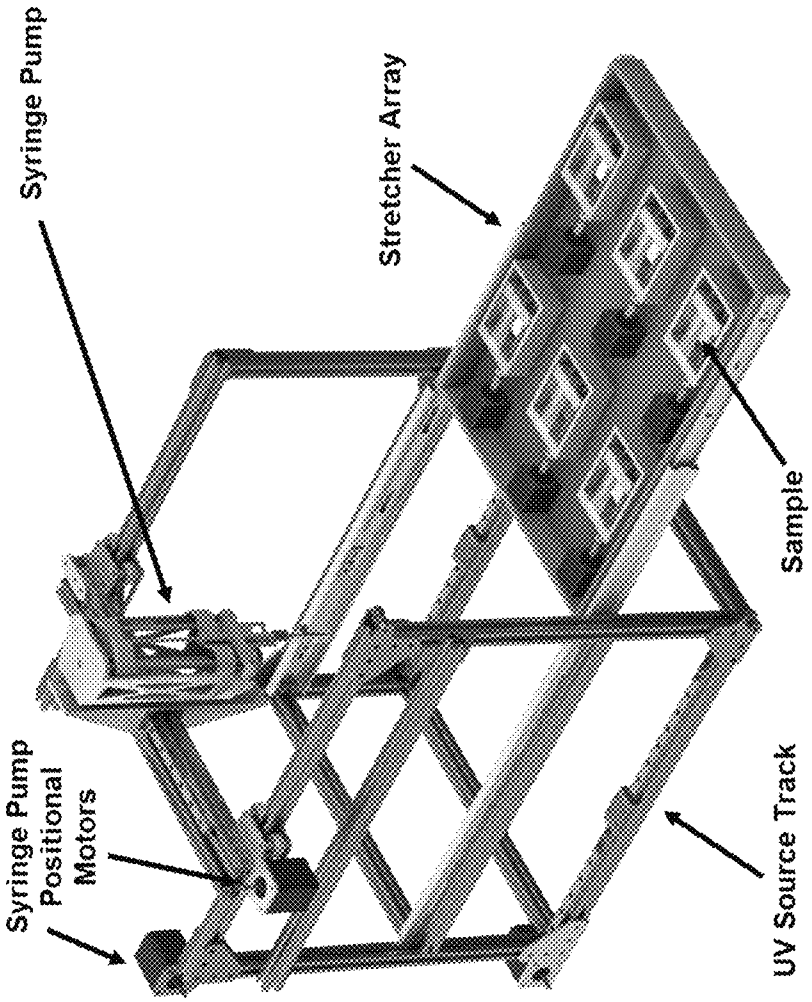

An exemplary system for preparing an ordered (e.g., patterned) cell-containing microarray is shown in FIGS. 31A and 31B. As depicted by the aerial view in FIG. 31A, a syringe pump (i.e., means for spraying (i.e., discharging, dispensing, etc.) a cell-containing composition) is movably positioned above a stretcher array (i.e., a means for mechanically straining an elastomeric substrate). The syringe pump (i.e., means for spraying (i.e., discharging, dispensing, etc.) a cell-containing composition) can be repositioned by any suitable means (e.g., positional motors, sliding tracks, levers, pulleys, etc.). Similarly, the stretcher array (i.e., a means for mechanically straining an elastomeric substrate) includes one or multiple stretcher assemblies and can be repositioned by any suitable means (e.g., positional motors, sliding tracks, levers, pulleys, etc.). Each stretcher assembly may include mechanical elements to grip or clamp portions of a substrate and to stretch and/or apply a strain to a secured substrate by moving (e.g., one or more of positional motors, sliding tracks, springs or other biasing elements, etc.) the gripping/clamping elements in a manner so as to provide a 1D stretch or strain, a 2D stretch or strain or an omnidirectional stretch or strain. As depicted by the side view in FIG. 31A, the spray distance can be adjusted by moving the syringe pump (i.e., means for spraying (i.e., discharging, dispensing, etc.) a cell-containing composition) up and down relative to the stretcher array.

The system depicted in FIG. 31A further comprises a UV source track (i.e., a light source), which is movably positioned below the stretcher array (i.e., a means for mechanically straining an elastomeric substrate). The UV source (i.e., light source) can be repositioned by any suitable means (e.g., positional motors, sliding tracks, levers, pulleys, etc.).

Examples of Non-Limiting Embodiments of the Disclosure

Embodiments, including aspects, of the present subject matter described herein may be beneficial alone or in combination, with one or more other aspects or embodiments. Without limiting the foregoing description, certain non-limiting embodiments of the disclosure numbered 1-42 are provided below. As will be apparent to those of skill in the art upon reading this disclosure, each of the individually numbered embodiments may be used or combined with any of the preceding or following individually numbered embodiments. This is intended to provide support for all such combinations of embodiments and is not limited to combinations of embodiments explicitly provided below:

(1) In embodiment (1) is presented a method for preparing an ordered cell-containing microarray, the method comprising process (A) or process (B):

(A) (i) providing an elastomeric substrate, (ii) modifying a surface of the elastomeric substrate to provide a surface-modified elastomeric substrate, (iii) spraying a cell-containing composition onto the surface-modified elastomeric substrate to provide a disordered cell-containing microarray, and (iv) applying a strain to the disordered cell-containing microarray to provide the ordered cell-containing microarray;

(B) (i) providing an elastomeric substrate, (ii) modifying a surface of the elastomeric substrate to provide a surface-modified elastomeric substrate, (iii) applying a strain to the surface-modified elastomeric substrate to provide a strained surface-modified elastomeric substrate, (iv) spraying a cell-containing composition onto the strained surface-modified elastomeric substrate to provide a disordered cell-containing microarray, and (v) relaxing the disordered cell-containing microarray to provide the ordered cell-containing microarray.

(2) In embodiment (2) is presented the method of embodiment (1), wherein modifying the surface of the elastomeric substrate comprises masking the elastomeric substrate and chemically modifying at least a portion of the surface of the elastomeric substrate to provide the surface-modified elastomeric substrate.

(3) In embodiment (3) is presented the method of embodiment (2), wherein chemically modifying at least a portion of the surface of the elastomeric substrate provides at least a portion of the surface of the elastomeric substrate that is hydrophilic.

(4) In embodiment (4) is presented the method of embodiment (2) or (3), wherein chemically modifying at least a portion of the surface of the elastomeric substrate provides at least a portion of the surface of the elastomeric substrate that enables assembly of disordered cell-containing microarray into ordered cell containing microarray by hydrophobicity contrast and promotes cell adhesion or is capable of attachment of a chemical moiety by chemically, thermally, and/or photolytically treating the surface-modified elastomeric substrate in the ordered cell-containing microarray.

(5) In embodiment (5) is presented the method of any one of embodiments (2)-(4), wherein chemically modifying at least a portion of the surface of the elastomeric substrate comprises oxidizing the surface.

(6) In embodiment (6) is presented the method of embodiment (5), wherein oxidizing the surface comprises treating the surface with ozone or plasma oxidation.

(7) In embodiment (7) is presented the method of any one of embodiments (2)-(6), wherein chemically modifying at least a portion of the surface of the elastomeric substrate comprises attaching to the surface of the elastomeric substrate a peptide-based adhesion promoter, a small molecule adhesion promoter, a (meth)acrylate-containing compound, a (meth)acrylamide-containing compound, a polyethylene glycol-containing compound, a fluorocarbon (e.g., fluorinated alkyl, perfluorinated alkyl, etc.), a NHS-ester-containing compound, a maleimide-containing compound, an azide-containing compound, an alkyne-containing compound, or any combination thereof.

(8) In embodiment (8) is presented the method of any one of embodiments (2)-(7), wherein chemically modifying at least a portion of the surface of the elastomeric substrate comprises attaching to the surface of the elastomeric substrate a peptide-based adhesion promoter.

(9) In embodiment (9) is presented the method of embodiment (8), wherein the peptide-based adhesion promoter is Arg-Gly-Asp (RGD), polylysine, polyarginine, polyhistidine, fibronectin, laminin, collagen, or a combination thereof.

(10) In embodiment (10) is presented the method of any one of embodiments (1)-(9), wherein the cell-containing composition is sprayed at a pressure of about 5 kPa to about 100 kPa.

(11) In embodiment (11) is presented the method of any one of embodiments (1)-(10), wherein the cell-containing composition is sprayed at a pressure of about 30 kPa to about 60 kPa.

(12) In embodiment (12) is presented the method of any one of embodiments (1)-(11), wherein the cell-containing composition is sprayed at a flow rate of about 10 $\mu Lmin^{-1}$ to 100 $\mu Lmin^{-1}$.

(13) In embodiment (13) is presented the method of any one of embodiments (1)-(12), wherein the cell-containing composition is sprayed at a flow rate of about 40 $\mu Lmin^{-1}$ to 80 $\mu Lmin^{-1}$.

(14) In embodiment (14) is presented the method of any one of embodiments (1)-(13), wherein the cell-containing composition is sprayed at a distance of about 1 cm to about 20 cm from the surface-modified elastomeric substrate or the strained surface-modified elastomeric substrate.

(15) In embodiment (15) is presented the method of any one of embodiments (1)-(14), wherein the cell-containing composition is sprayed at a distance of about 5 cm to about 15 cm from the surface-modified elastomeric substrate or the strained surface-modified elastomeric substrate.

(16) In embodiment (16) is presented the method of any one of embodiments (1)-(15), wherein the cell-containing composition comprises a liquid media.

(17) In embodiment (17) is presented the method of embodiment (16), wherein the liquid media comprises a buffer, a suspension media, a culture media, or a combination thereof.

(18) In embodiment (18) is presented the method of any one of embodiments (1)-(15), wherein the cell-containing composition comprises a gel media or gel media precursor.

(19) In embodiment (19) is presented the method of embodiment (18), wherein the gel media or gel media precursor comprises a hydrogel or a hydrogel precursor.

(20) In embodiment (20) is presented the method of any one of embodiments (1)-(19), wherein applying the strain to the disordered cell-containing microarray or the surface-modified elastomeric substrate comprises stretching the elastomeric substrate.

(21) In embodiment (21) is presented the method of embodiment (20), wherein the elastomeric substrate is stretched uniaxially, biaxially, or omnidirectionally.

(22) In embodiment (22) is presented the method of any one of embodiments (1)-(21), wherein the method further comprises attaching the cell-containing composition to the surface-modified elastomeric substrate in the ordered cell-containing microarray by chemically, thermally, and/or photolytically treating the surface-modified elastomeric substrate in the ordered cell-containing microarray.

(23) In embodiment (23) is presented the method of embodiment (22), wherein the cell-containing composition is attached to the surface-modified elastomeric substrate in the ordered cell-containing microarray by photolytically treating the surface-modified elastomeric substrate in the ordered cell-containing microarray.

(24) In embodiment (24) is presented the method of any one of embodiments (1)-(23), wherein the method further comprises transferring the ordered cell-containing microarray to a cell culture media to induce and/or sustain growth of a cell.

(25) In embodiment (25) is presented the method of any one of embodiments (1)-(24), wherein the elastomeric substrate comprises a silane-based material.

(26) In embodiment (26) is presented the method of embodiment (25), wherein the elastomeric substrate comprises polydimethylsiloxane (PDMS).

(27) In embodiment (27) is presented the method of any one of embodiments (1)-(26), wherein the cell-containing composition comprises animal cell culture, plant tissue culture, tissue culture, organ culture, or a combination thereof.

(28) In embodiment (28) is presented the method of any one of embodiments (1)-(27), wherein the cell-containing composition comprises somatic cells (e.g., healthy or cancerous), stem cells, or a combination thereof.

(29) In embodiment (29) is presented the method of any one of embodiments (1)-(28), wherein the ordered cell-containing microarray is a two-dimensional microarray.

(30) In embodiment (30) is presented the method of any one of embodiments (1)-(29), wherein the ordered cell-containing microarray is a three-dimensional microarray.

(31) In embodiment (31) is presented a system for preparing an ordered cell-containing microarray according to any one of embodiments (1)-(30).

(32) In embodiment (32) is presented a system for preparing an ordered cell-containing microarray comprising a means for spraying a cell-containing composition and a means for mechanically straining an elastomeric substrate.

(33) In embodiment (33) is presented the system of embodiment (32), wherein the means for spraying a cell-containing composition is movably positioned above the means for mechanically straining an elastomeric substrate.

(34) In embodiment (34) is presented the system of embodiment (32) or (33), wherein the means for spraying a cell-containing composition comprises an inlet for receiving a cell-containing composition, an inlet for receiving a pressurized gas, and an outlet for spraying droplets (e.g., microdroplets) comprising the cell-containing composition.

(35) In embodiment (35) is presented the system of embodiment (34), wherein the outlet for spraying droplets (e.g., microdroplets) comprising the cell-containing composition is movably positioned about 1 cm to about 20 cm above the means for mechanically straining an elastomeric substrate.

(36) In embodiment (36) is presented the system of embodiment (35), wherein the outlet for spraying droplets (e.g., microdroplets) comprising the cell-containing composition is movably positioned about 5 cm to about 15 cm above the means for mechanically straining an elastomeric substrate.

(37) In embodiment (37) is presented the system of any one of embodiments (32)-(36), wherein the means for spraying a cell-containing composition is capable of spraying the cell-containing composition at a pressure of about 5 kPa to about 100 kPa.

(38) In embodiment (38) is presented the system of embodiment (37), wherein the means for spraying a cell-containing composition is capable of spraying the cell-containing composition at a pressure of about 30 kPa to about 60 kPa.

(39) In embodiment (39) is presented the system of any one of embodiments (32)-(38), wherein the means for mechanically straining an elastomeric substrate stretches the elastomeric substrate.

(40) In embodiment (40) is presented the system of embodiment (39), wherein the means for mechanically straining an elastomeric substrate stretches the elastomeric substrate uniaxially, biaxially, or omnidirectionally.

(41) In embodiment (41) is presented the system of any one of embodiments (32)-(40), wherein the system further comprises a light source.

(42) In embodiment (42) is presented the system of embodiment (41), wherein the light source is movably positioned below the means for mechanically straining an elastomeric substrate.

EXAMPLES

These following examples further illustrate the invention but, of course, should not be construed as in any way limiting its scope.

Unless indicated otherwise, the following materials were utilized in the following examples. Sylgard® 184 silicone elastomer kit (Dow Corning Co.) and acrylonitrile butadiene styrene (ABS-plus) model material (Stratasys Ltd.) for 3D printing were purchased from the noted vendors, and used as received. 2-propanol (CAS #67-63-0), ethanol (CAS #64-17-5), glycerol (CAS #56-81-5), Triton X-100 (CAS #9002-93-1), Poly-D-Lysine solution, Poly-L-lysine-FITC labeled, sodium alginate, and calcium chloride (CAS #10043-52-4) were purchased from Sigma-Aldrich Co. LLC. Gas tight syringes (1001 Model from Hamilton®) and 26 Ga removable needles (51 mm length, blunt tip, point style 3) were purchased from Sigma-Aldrich Co. LLC. Masterflex Tygon® tubing (Lab E-3603 L/S 13) was purchased from Cole-Parmer® and Polyethylene Tubing (BTPE-60 by Instech Laboratories, Inc.) was purchased from Fisher Scientific. PVDF barbed plastic Tee connectors (High-Purity, 1/16") were purchased from McMaster-Carr®.

Hanks' Balanced Salt Solution (HBSS), N-2-hydroxyethylpiperazine-N-2-ethane sulfonic acid (HEPES) buffer, Calcein AM, Propidium Iodide, Alexa Fluor™ 488 Phalloidin, Hoechst 33342 trihydrochloride trihydrate, CellTracker™ green CMFDA (5-chloromethylfluorescein diacetate), CellTracker™ orange CMRA and all cell culture reagents were purchased from ThermoFischer Scientific, stored upon arrival, and used as indicated by the supplier.

Unless indicated otherwise, the following methods were utilized in the following examples.

Polydimethylsiloxane (PDMS) Substrate Fabrication

Polydimethylsiloxane (PDMS) films were prepared using a 10:1 base to curing agent ratio, by pouring the degassed prepolymer mixture onto 4-inch silicon wafers (University Wafer Inc.). A universal applicator (Zehntner GmbH Testing Instruments, Switzerland) was used to obtain elastomeric films with a thickness of 500 μm. The PDMS was cured for 48 hours at 60° C. in a convection oven, and the resulting films were cut into 30 mm×6 cm strips. The strips were stirred in ethanol for an additional 48 hours at room temperature to remove un-crosslinked monomers. After rinsing with deionized water, we the PDMS strips were first dried under pressurized nitrogen and then inside a vacuum pump for 1 hour to remove any excess ethanol.

Surface Functionalization/Micropatterning of Elastomeric Films

Elastomeric substrates were oxidized in an oxygen plasma chamber (Plasma Etch Inc., Carson City, Nev., Model #PE-25 Series) for 10 seconds at a power of 15 W, and at ~201.1 mTorr of $O_2$. Prior to cell deposition, native or oxidized PDMS samples were incubated in PBS for 1 hour at 37° C., rinsed with filtered Millipore water, and dried.

For the synthesis of wettability micropatterns, MIMIC masks were placed onto the PDMS surface before the oxidation process. After removing the masks, the samples were immersed in a poly-L-lysine solution (50 μg/mL in PBS) for 1 hours at 37° C. and rinsed them with Millipore water and dried.

Cell Culture

The human epidermoid carcinoma cell line A-431 was obtained and the cells were cultured in Dulbecco's modified Eagle's medium (DMEM) supplemented with 10% fetal bovine serum, and 1% Penicillin Streptomycin (10,000 units $mL^{-1}$), in 75 $cm^2$ flasks at 37° C. in a humidified atmosphere with 5% carbon dioxide.

Cell Sample Preparation

Cell lines at 90% confluency were detached from the cell culture flask using trypsin treatment (0.25% Trypsin-EDTA) and resuspended in 5 mL DMEM. After a centrifugation (100 g, 5 minutes) and a rinsing step with PBS, the supernatant was discarded and the cell lines were re-suspended in DMEM supplemented with HEPES (20 mM) and 5 wt. % Glycerol, which had been pre-warmed at 37° C. to a final concentration of $2\times10^6$ cells/mL.

Spraying, Aerosol Droplet Formation, and Delivery

The spraying device was loaded with 500 μL of cell suspension and was secured on a syringe pump. Cell spraying was performed at 0.01-0.1 mL/min and 0-70 kPa with an approximate distance of 15 cm between the spray nozzle and the samples. The samples and spraying device were placed in a humidity chamber, equipped with a humidity sensor (RH>90%) to prevent the evaporation of microdroplets.

Stretching and Droplet Assembly

A stretcher device, as shown in FIG. 14, was used to apply mechanical strain to PDMS strips using solid object printing. The components were designed in a CAD program (Inventor Professional by Autodesk Inc.) and printed in ABS using a 3D-printer (Dimension Elite, Stratasys Ltd.). A uniaxial strain was applied by stretching the substrate along its length (L). An increase in the initial length (L) to a final length (L') would provide a strain $\varepsilon=(L'-L)/L$.

Microscopic Characterization

Bright field and fluorescence microscopy of the functionalized wettability patterns was performed using a Zeiss microscope (Axio Scope.A1) equipped with an AxioCam MRc5 camera, and the ZEN-Pro software (version 2.3).

Fluorescence Cell Labeling and Imaging

To assess cell viability, living cells were labeled with Calcein-AM (0.5 μM, GFP) and dead cells were labeled with Propidium Iodide (3 μM, TRITC). Cells were incubated in the labeling solution for 30 minutes at 37° C. The cells were then incubated in DMEM at 37° C. prior to imaging. The number of live green cells ($N_{Live}$) and the number of dead red cells ($N_{Dead}$) were counted for each sample through fluorescence imaging to obtain: Viability (%)=$N_{Live}/(N_{Live}+N_{Dead})*100$. A total of 6 samples were performed for each set of spraying conditions during two independent experiments and an average of 2,000 cells were counted for each sample.

To monitor the content of sprayed droplets and the spatial distribution of assembled cell arrays on PDMS surfaces, living cells were labeled with CellTracker™ green and orange. These dyes provide bright intensity signals and are retained in live cells for up to 72 h, allowing for extended cell monitoring through fluorescence microscopy. Prior to cell spraying and assembly, cells were incubated in the labeling solution (5 μM in serum free DMEM medium) for 30 minutes at 37° C., washed with PBS, suspended in cell culture media supplemented with HEPES+glycerol and loaded inside the spraying device. To prevent photobleaching, cell suspensions labeled with CellTracker™ green and orange dyes were kept away from light.

Imaging of the labeled cells was performed using an epi-fluorescence microscope (Nikon Eclipse 80i) equipped with a high speed CCD camera (CoolSNAP HQ2, Photometrics, Roper Scientific—Princeton Instruments), a mercury lamp (HGFIL Lampe 130 W), and adequate filter sets. Fluorescence images for each set of filters were recorded using NIS Elements Imaging Software (Advanced Research, Nikon), and ImageJ software (National Institutes of Health, USA) was used for image analysis.

The fluorescence labeling of the actin filaments and the nuclei was performed after 24 hours or 48 hours of cell culture. In that regard, the cells were washed twice with PBS and then were fixed on the PDMS surfaces using formaldehyde solution (4% in PBS) for 10 minutes at room temperature. Following an additional washing step in PBS, the cells were permeablized with 0.1% Triton X-100 for 3-5 minutes. After washing, 200 μL of A-488 conjugated fluorescent phallotoxin solution (5 units/mL) was applied on top of each sample and the sample was covered with a coverslip for 20 minutes of incubation with the staining solution. Finally, the nuclei were stained blue with Hoechst solution (1/1000 dilution in PBS) for 10 minutes. Samples were washed and covered with mounting medium and a glass cover slip before confocal imaging.

Contact Angle Measurements

Side view photographs for measuring droplet contact angles were taken on a Theta goniometer (Biolin Scientific). An average of 10 nanopore water droplets of 1 μL were deposited on PDMS surfaces with different coatings. Measurements were repeated on three different samples. The Young-Laplace equation was used to fit the shape of each droplet after performing the base line correction and the average contact angle was calculated from both sides of the drop.

Example 1

This example provides an exemplary procedure for the generation of microfluidic-based aerosol droplets for use in cell-in-droplet deposition.

The reported design of the V-EASI spraying device was modified to produce a custom apparatus that was suitable for the generation and delivery of cell-loaded aerosol microdroplets to the assembly substrates. Specifically, a system which provided controlled mixing of two fluid phases, an aqueous solution (e.g., a buffer or cell suspension) and a pressurized gas (e.g., air or nitrogen) at the exit of the spraying nozzle. See FIG. 1. The effect of the following physical parameters on the control of droplet size distribution, and surface coverage were examined for optimization of the spraying process: flow rate (Q), pressure (P), nozzle size aperture (a), and the nozzle to sample distance (d).

Calibrated needles were used to set the nozzle diameter (a=260 μm) and a moving stage to control the distance (d=15 cm). A syringe pump and a pressure regulator were used to independently modify the applied pressure (P=0 to 70 kPa) and flow rate (Q=10 $\mu Lmin^{-1}$ to 100 $\mu Lmin^{-1}$) to achieve the desired spray pattern. In addition, the fluid properties (e.g., viscosity, surface tension, vapor pressure, biocompatibility) were evaluated to enable droplet formation with controlled droplet size and to prevent evaporation. To this end, cell culture media supplemented with HEPES and glycerol was used as cell suspension media during spray to stabilize the pH under atmospheric $CO_2$ levels (<0.05%) and to prevent droplet evaporation. To further reduce the risk of liquid evaporation, which could alter the cell media composition and reduce cell viability, the spraying experiment was performed inside a high humidity chamber at >90% relative humidity (RH).

The droplet size distribution was measured after spraying a cell suspension solution onto native hydrophobic PDMS surfaces, using three different pressures (34, 48, 62 kPa, equivalent of 6, 8 and 10 PSI), and maintaining the other parameters constant. See FIGS. 2A-2C. As is apparent from FIGS. 2A-2C, a decrease in the average droplet diameter and a narrower size distribution was observed for increasing pressures.

The cells were labeled with CellTracker™ green to differentiate empty droplets from droplets that contained cells on the same surfaces. An exemplary fluorescence micrograph for samples sprayed with 48 kPa is shown in FIG. 3. The number of cell containing droplets were determined for each of the three different pressures (34, 48, 62 kPa, equivalent of 6, 8 and 10 PSI), and the results are shown in FIGS. 2A-2C.

Figure 2A:
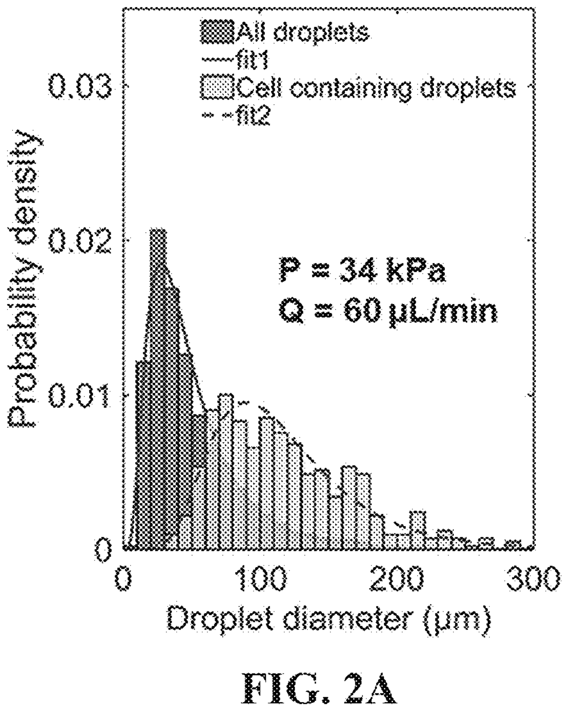
FIGS. 2A-2C show the size distribution for cell-loaded microdroplets delivered onto native PDMS surfaces, including the probability distribution for microdroplets with and without cells, for air pressures of 34 kPa, 48 kPa, and 62 kPa, respectively.
Figure 2B:
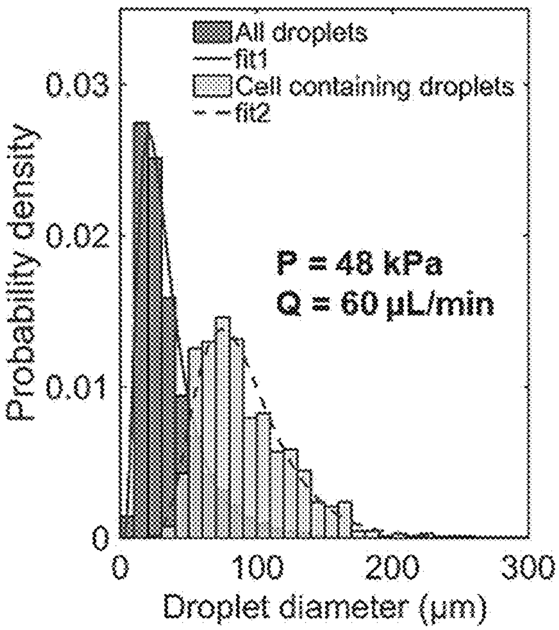
Figure 2C:
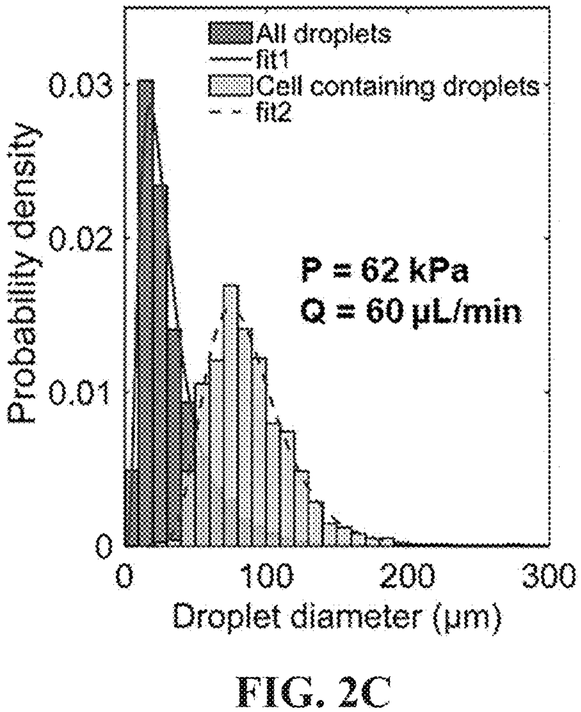
Figure 3:
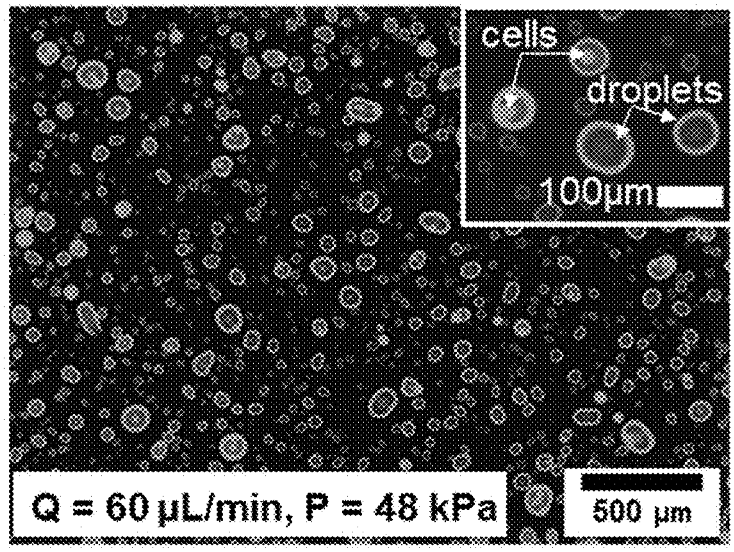
FIG. 3 shows a fluorescence micrograph of microdroplets with cell cargo, which have been sprayed onto a native PDMS surface at 60 μL/min and 48 kPa, and have been labeled with CellTracker™. The magnified view in the upper right of FIG. 3 shows empty and cell-loaded droplets.

As is apparent from the results set forth in FIGS. 2A-2C, for the samples sprayed with 48 kPa of pressure, even though the average size for the total droplet population is 36±25 μm (mean±S.D.), equivalent to 12±4 ρL in volume, only droplets above 40 μm in diameter contained cells. See FIG. 2B. Without wishing to be bound by any particular theory, it is believed that this can be explained by the average size for the A431 cells (10-20 μm) and cell-triggered Rayleigh-Plateau instabilities during droplet generation. The distribution of cell containing droplets was evaluated and an average droplet diameter of 91±35 μm (coefficient of variation, C.V.=38%, equivalent to 197±11 ρL in volume) was measured at 48 kPa of pressure. Using higher pressures resulted in narrower size distributions for cell-containing droplets (88±30 μm, C.V.=34%, equivalent to 178±7 ρL in volume, for 62 kPa in FIG. 2C), while lower pressures produced the opposite effect (117±50 μm, C.V.=43%, equivalent to 419±33 ρL in volume, for 34 kPa in FIG. 2A).

Figure 4:
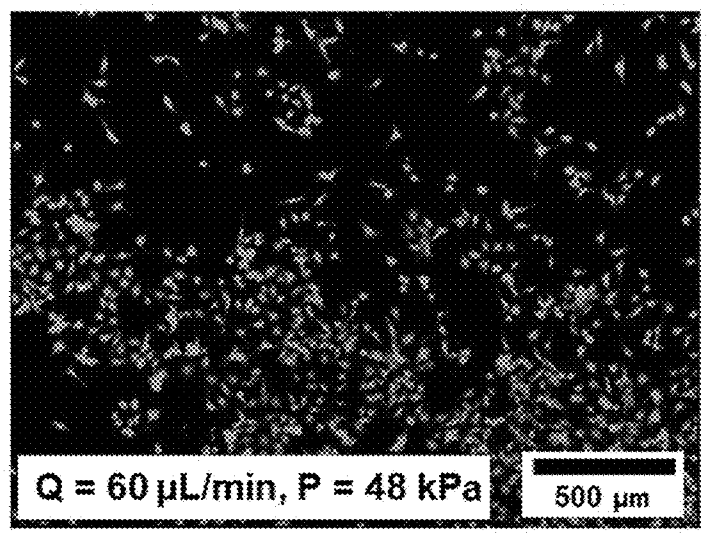
FIG. 4 shows a fluorescence micrograph of a live/dead assay of cells that have been sprayed onto plasma treated PDMS surfaces at 60 μL/min and 48 kPa and incubated in cell growth media for 24 hours. The live cells have been labeled with calcein-AM (green) and the dead cells have been labeled with propidium iodide (red).
Figure 5:
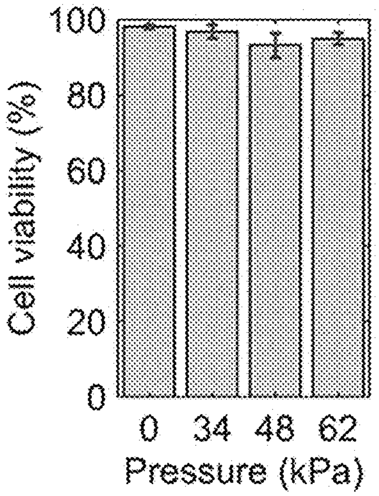
FIG. 5 provides a bar graph showing the cell viability measurements for cell-loaded microdroplets delivered onto plasma treated PDMS surfaces at 60 μL/min and 0 kPa, 34 kPa, 48 kPa, or 62 kPa.

To evaluate the effect of shear stress on cell damage during the spraying process, the cell viability was assessed 24 hours after impact with the PDMS surfaces where the cells were incubated in cell growth media following the spray deposition procedure (at 37° C. and 5% $CO_2$). Two-color fluorescence-based cell viability assay was used to label and count live cells with calcein-AM (green) and dead cells with propidium iodide (red). An exemplary live/dead assay for the samples sprayed with 48 kPa of pressure is shown at FIG. 4. A viability of 93±3% for 48 kPa of pressure at a flow rate of 60 $\mu Lmin^{-1}$ was calculated. The viability data remained stable for all spraying conditions. See, for example, FIG. 5. The approximate viability rate of 93% or greater indicates that the foregoing technique can be applicable to a host of cell types.

Example 2

This example provides an exemplary procedure for the generation of a micro-assembly of cells-in-droplets (μACD).

Figure 6:
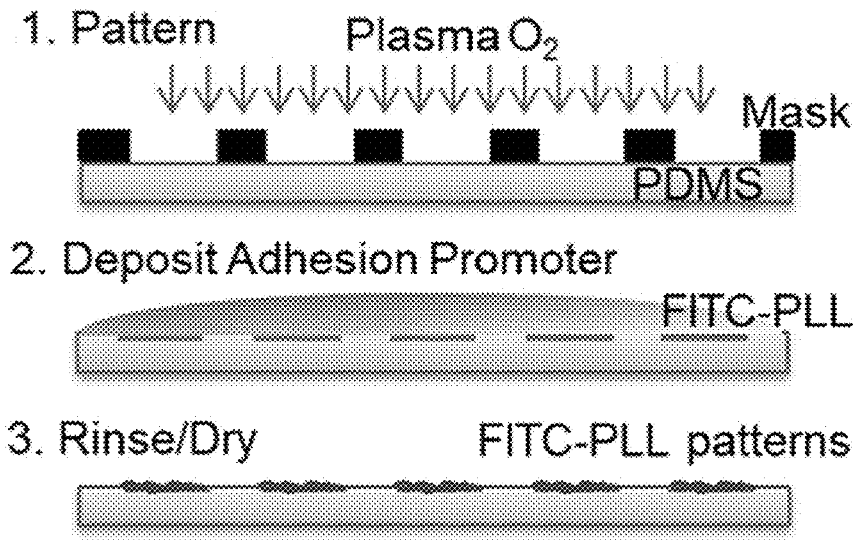
FIG. 6 shows an exemplary synthesis of wettability micropatterns with cell adhesion promoting matrix on elastomeric films.
Figure 7:
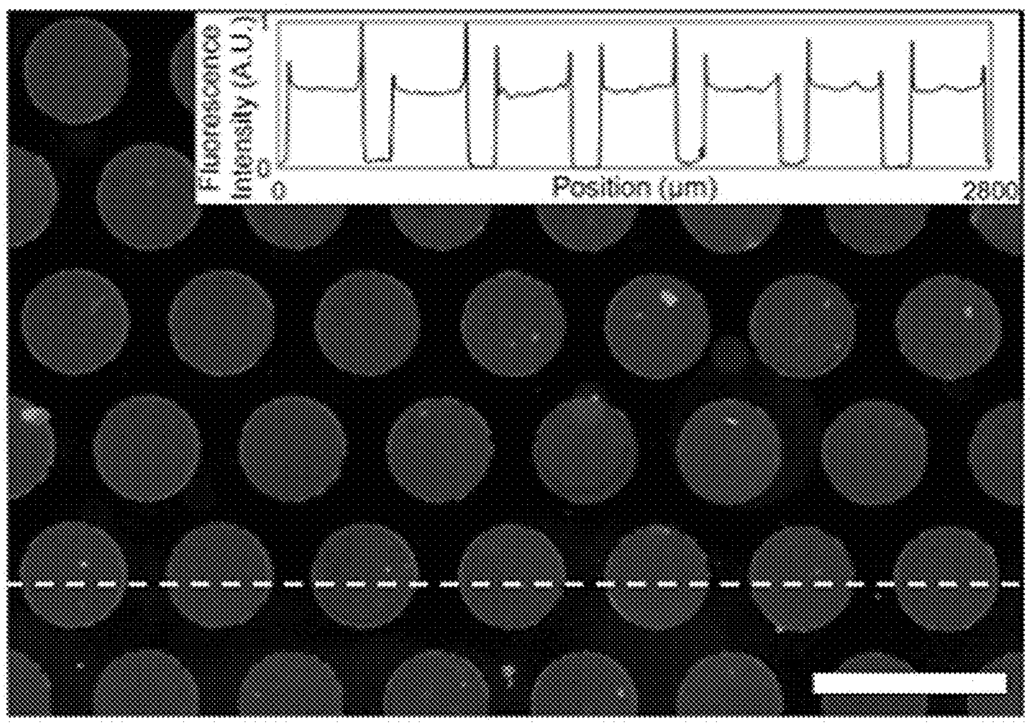
FIG. 7 shows a fluorescence micrograph of a fluorescein isothiocyanate (FITC)-labeled poly-L-lysine (PLL) micropattern. The inlay in the upper right corner shows the fluorescence plot profile across the dotted white line.

In general, the generation of the ordered array of cells included three main steps: i) the fabrication of an array of micropatterns on the surface of an elastomeric film; ii) the generation and deposition of cell-loaded aerosol microdroplets; and iii) the assembly of the microdroplets into order arrays for placement of the cell cargo into the desired patterns. FIG. 6 provides an exemplary synthesis of wettability micropatterns with cell adhesion promoting matrix on elastomeric films. More particularly, the wettability micropatterns were synthesized by applying $O_2$ plasma to PDMS films through a polymer mask (FIG. 6, step 1), and then immersing the oxidized films in a FITC-conjugated Poly-L-Lysine (FITC-PLL) solution (FIG. 6, step 2). The films were rinsed and dried to obtain the desired PLL micropatterns for localized cell adhesion (FIG. 6, step 3). As demonstrated by the fluorescence micrograph and corresponding fluorescence intensity provided in FIG. 7, a preferential adsorption of PLL to the hydrophilic regions (oxidized, hydroxyl terminated-PDMS) and a limited non-specific adsorption of PLL to hydrophobic regions (native, methyl-terminated PDMS) was observed.

Figure 8:
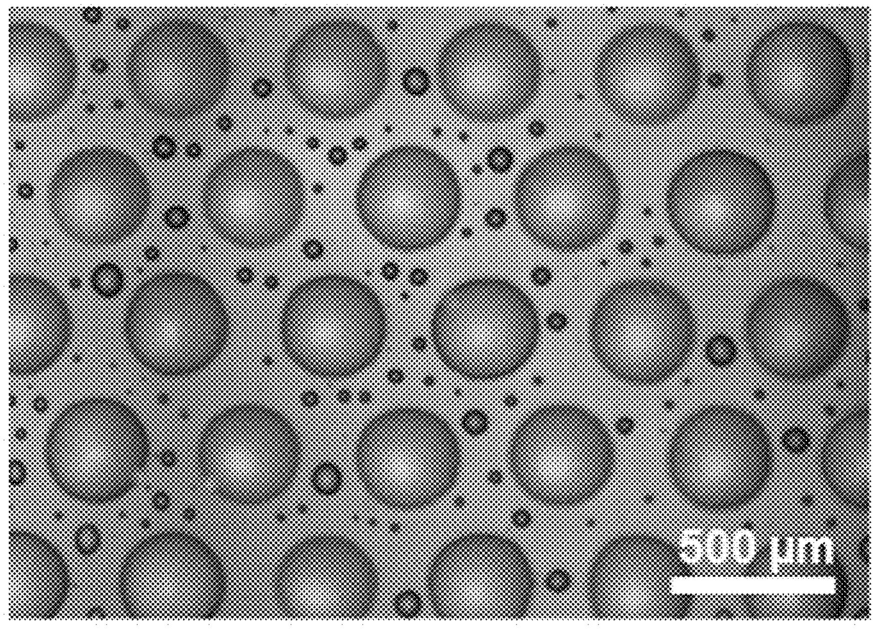
FIG. 8 provides and image of aqueous droplets, which include phosphate buffered saline (PBS), fluorescein isothiocyanate (FITC), and 10% glycerol, assembled on a poly-L-lysine (PLL) micropattern.

Contact angle measurements (average of 10 water droplets, 1 μL in volume) were performed to quantify the differences in wettability for both the hydrophilic and hydrophobic regions after the PLL functionalization. A high contrast in wettability was obtained when comparing native ($\theta=114°\pm2°$) and plasma oxidized ($\theta=12°\pm5°$) PDMS surfaces coated with PLL (50 $\mu gmL^{-1}$), showing that this fabrication procedure was compatible with the confinement of liquid droplets inside the hydrophilic regions, as required for droplet assembly, as evidenced by FIG. 8.

Figure 9:
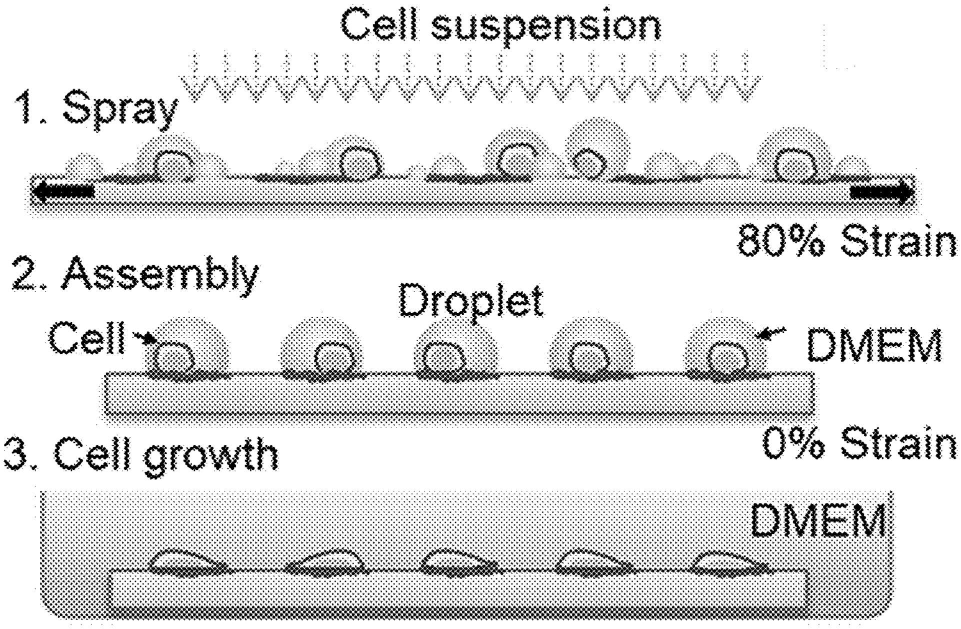
FIG. 9 shows an exemplary synthesis for cell/droplet assembly on PDMS-supported poly-L-lysine (PLL) micropatterns via mechanical actuation.

Next, cell-loaded aerosol microdroplets were generated using the procedures described above, while applying a mechanical strain to the functionalized surfaces ($\varepsilon=80\%$). The stretching process is depicted in FIG. 9, and more particularly, FIG. 9, step 1. The coalescence and assembly was observed for the generated picoliter droplets on the hydrophilic patterns upon strain release (FIG. 9, step 2), leading to the formation of microscale droplet arrays.

Figure 12:
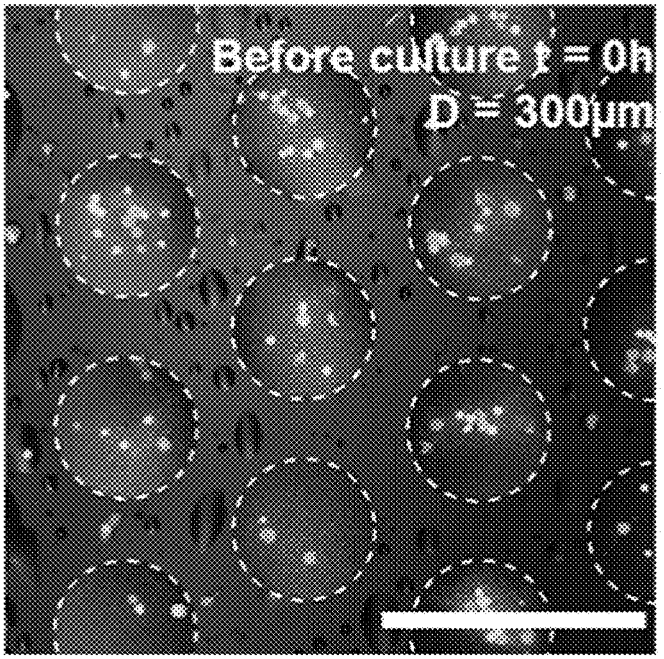
FIG. 12 shows a fluorescence micrograph (300 μm patterns and [C]=1×) for assembled microdroplets containing living cells (CellTracker™ orange staining) after strain release and before transferring to cell culture flask.

Using the spraying device shown at FIG. 1 and the following operating conditions: a=260 μm, d=15 cm, P=48 kPa, and Q=60 $\mu Lmin^{-1}$, a spray delivery time of 60 to 120 seconds was used to obtain surface areas of 1 to 3 $cm^2$ containing circular patterns with 150 to 300 μm in diameter. Without wishing to be bound by any particular theory, it is believed that using longer spraying times would result in uncontrolled droplet coalescence on the surfaces, with "over-filled" patterns and "bridging" defects, deteriorating the quality of the assembled cell arrays. The resulting samples were transferred to a cell culture flask and added cell culture media to allow for cell attachment and proliferation (FIG. 9, step 3). The cells were stained with CellTracker™ orange before spraying and observed efficient droplet and cell assembly inside the hydrophilic PLL micropatterns that were labeled in green (FITC staining), demonstrating the compatibility of this procedure with fluorescence microscopy for real time monitoring of live cells. The results are shown in FIG. 12.

Figure 10A:
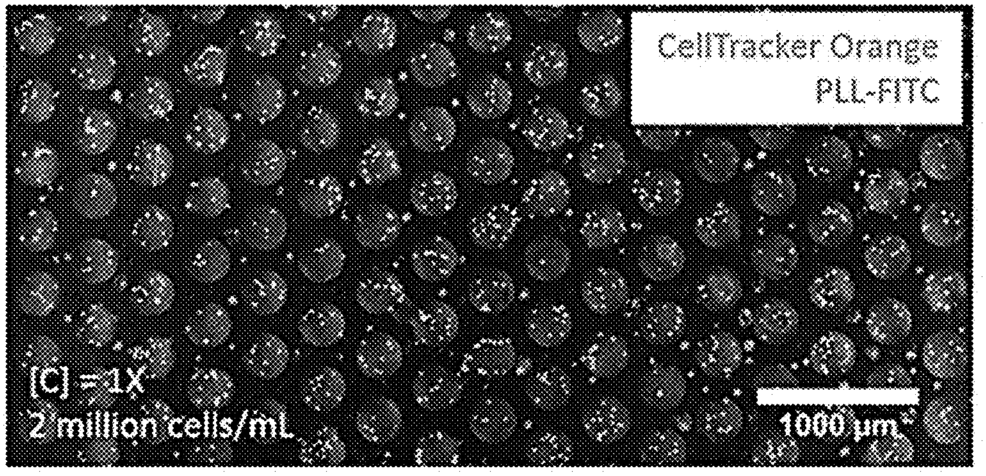
FIGS. 10A-10C show fluorescence micrographs for the distribution of number of cells per well for 300 μm patterns at concentrations of [C]=1× (FIG. 10A), [C]=0.5× (FIG. 10B), and [C]=0.25× (FIG. 10C). Patterns are stained with fluorescein isothiocyanate (FITC)-labeled poly-L-lysine (PLL) and the cells are stained with CellTracker™ orange.
Figure 10B:
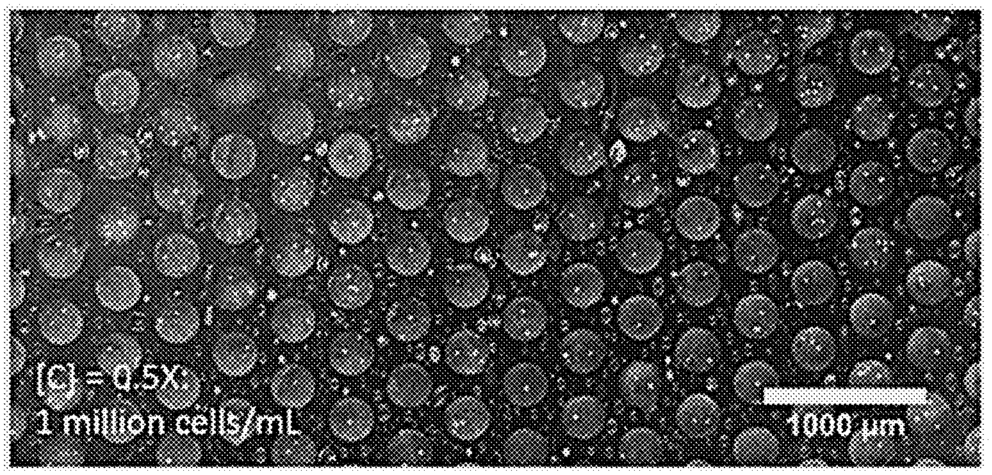
Figure 10C:
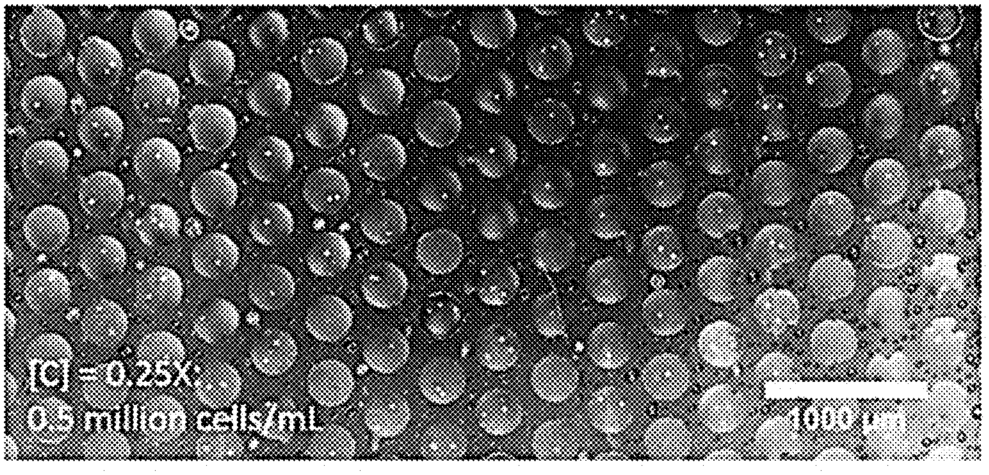

The distribution of cells inside the assembled liquid droplets was evaluated. First, a constant pattern size (D=300 μm in diameter) was used while the cell concentration was varied ([C]=1×, 0.5× and 0.25× equivalent of 2 million, 1 million and 500,000 cells/mL). Fluorescent micrographs were generated with the patterns stained using fluorescein isothiocyanate (FITC)-labeled poly-L-lysine (PLL) and the cells stained using CellTracker™ orange, and the results are set forth in FIGS. 10A-10C. The probability density was calculated using the fluorescent micrographs provided at FIGS. 10A-10C, and the results are shown in FIG. 11A.

Figure 11A:
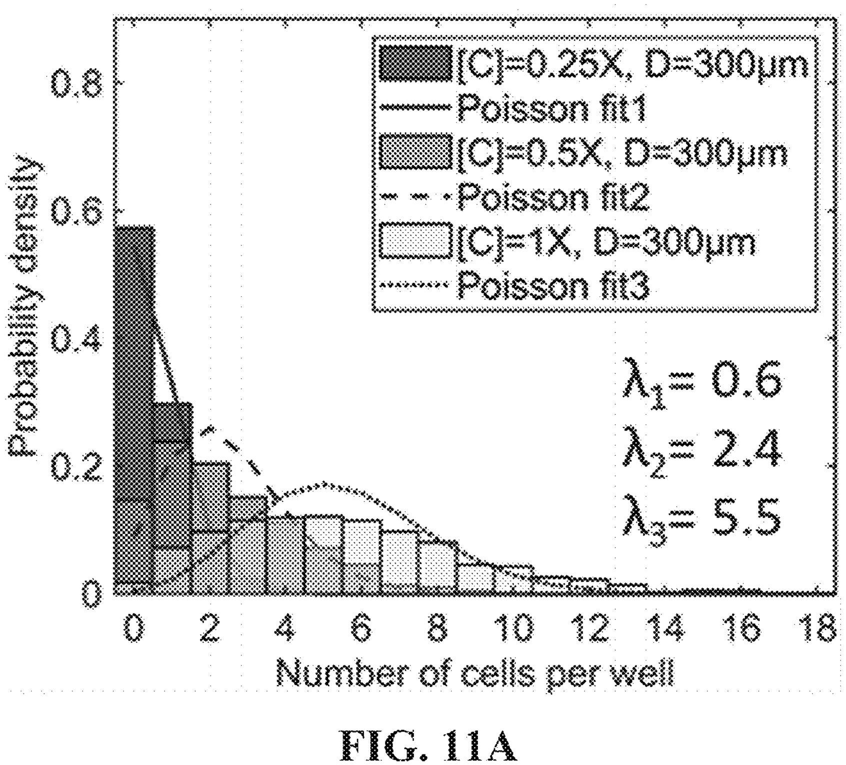
FIGS. 11A and 11B show probability density of number of cells per well for different pattern sizes and cell concentrations.
Figure 11B:
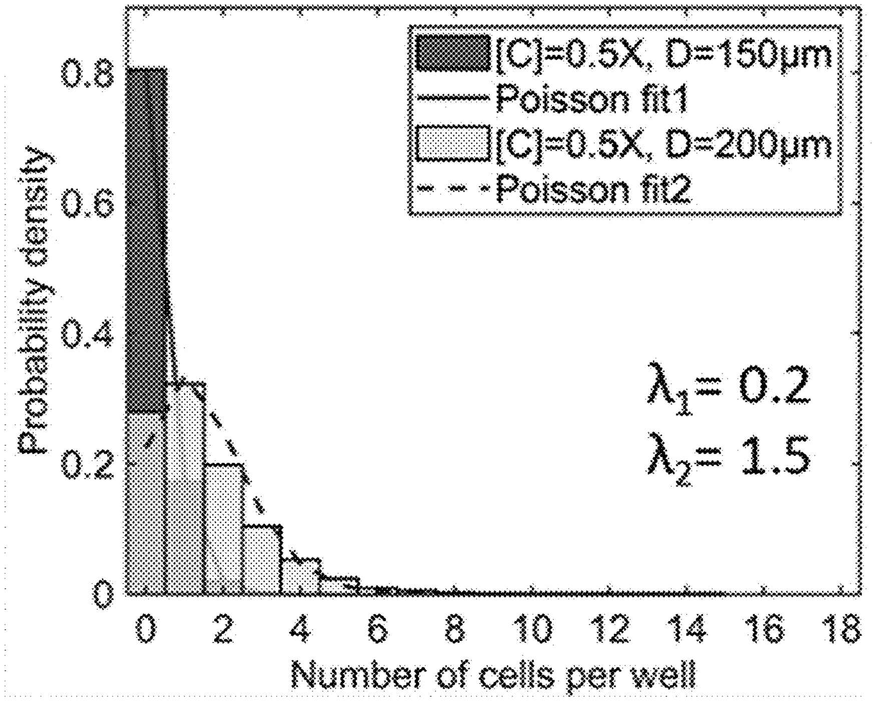

Using the results set forth in FIG. 11A an average of 5±3 cells/well was measured for the highest cell concentration with most wells occupied (>95%), and a broad cell distribution. For the lowest concentration, 30% of wells with a single cell was obtained, but most wells were empty, following a Poisson distribution ($\lambda1=0.6$). A similar trend was observed when varying the pattern size (diameter D=300, 200 and 150 μm, with solid fraction areas of 0.45, 0.40 and 0.33 respectively) and maintaining the cell concentration constant ([C]=0.5×). The results for pattern sizes of 200 and 150 μm are set forth in FIG. 11B. Based on the distribution of droplet size and the distribution in size of cell-containing droplets set forth in FIGS. 2A-2C and 11A, it is clear that the spray nozzles used deliver many small droplets (<30 μm diameters) that do not contain cells and relatively fewer large droplets (80-100 μm diameters) that contain a cell. The assembly procedure, initiated through release of tension, collects multiple droplets into a single well, where the droplet count is determined by the array geometry, as demonstrated by FIG. 9. By tuning the cell concentration, the array geometry, and the nozzle pressure, the number of cells per well was tuned, as evidenced by FIG. 11B.

Figure 13A:
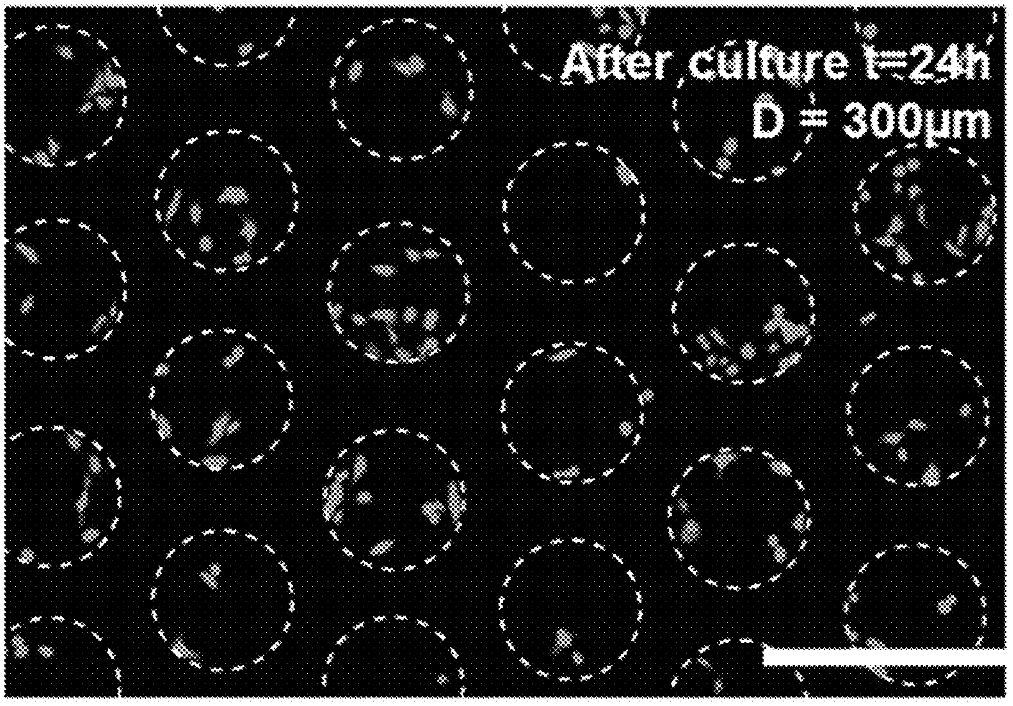
FIGS. 13A and 13B show fluorescence micrographs of live cells in 300 μm patterns after transfer to cell culture flask and 24 h and 48 h of culture for FIG. 13A (calcein-AM green staining) and FIG. 13B (CellTracker™ orange staining), respectively.
Figure 13B:
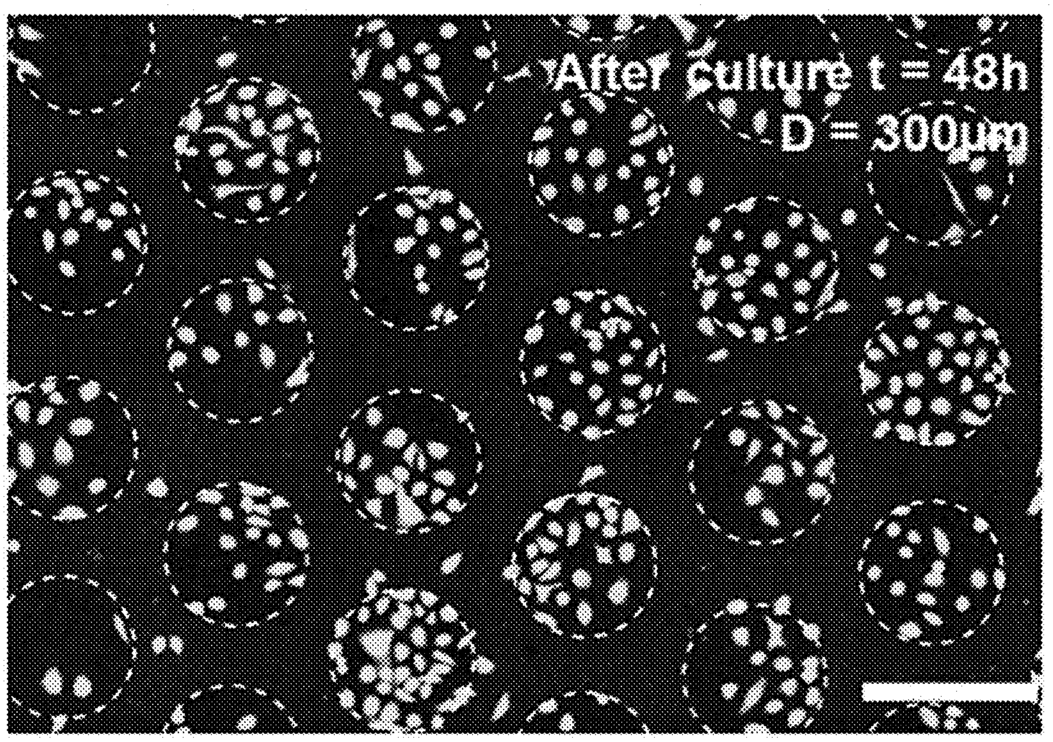

Following the spray delivery and assembly of cells onto different patterns, the samples were transferred to a cell culture flask and were allowed to proliferate inside an incubator. The cell viability was preserved (>90%) during the assembly process and the cells were confined inside the patterns after 24 to 48 hours, as evidenced by FIGS. 13A and 13B.

Example 3

This example demonstrates that the procedure for the generation of a micro-assembly of cells-in-droplets (μACD) provides a regular array of cells with defined cell colonies inside each pattern.

Microarray patterns (125 μm patterns and [C]=1× and 300 μm patterns and [C]=1×) containing cells were fixated and stained (nuclei in blue with Hoechst and actin filaments in green using A-488 conjugated phallotoxins) after 24 hours of culture, and the resulting samples were imaged with fluorescence imaging. The results for the 125 μm pattern and the 300 μm pattern are set forth in FIGS. 15A and 16, respectively. FIG. 15B provides a zoom-in view of the white box shown in FIG. 15A.

Figure 15A:
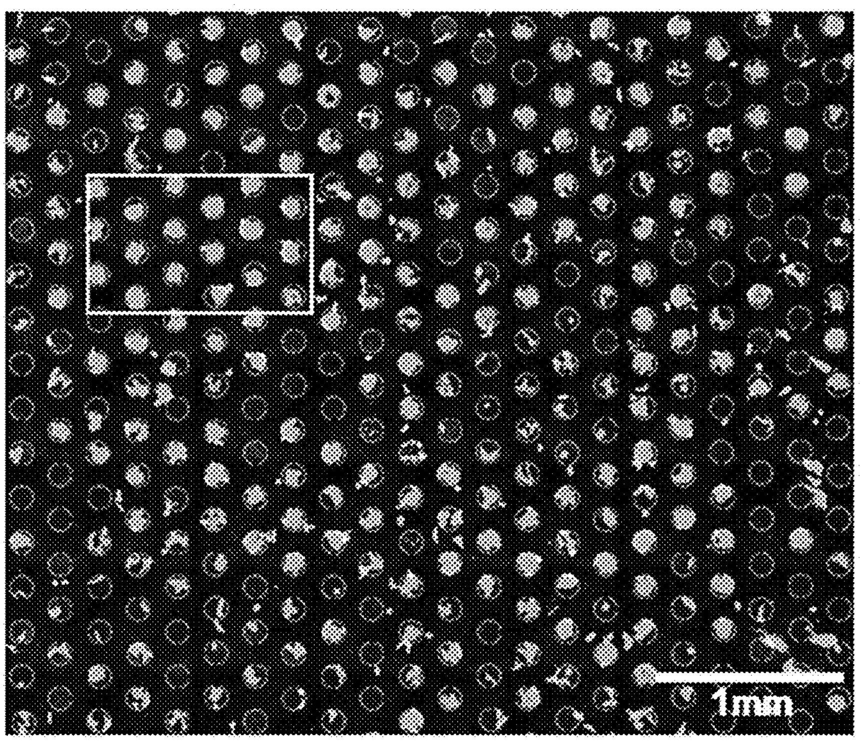
FIGS. 15A and 15B show a fluorescence micrograph (125 μm patterns and [C]=1×) for assembled microdroplets containing living cells with the nuclei labeled with Hoechst (blue) and actin filaments labeled with phallotoxins (green).
Figure 15B:
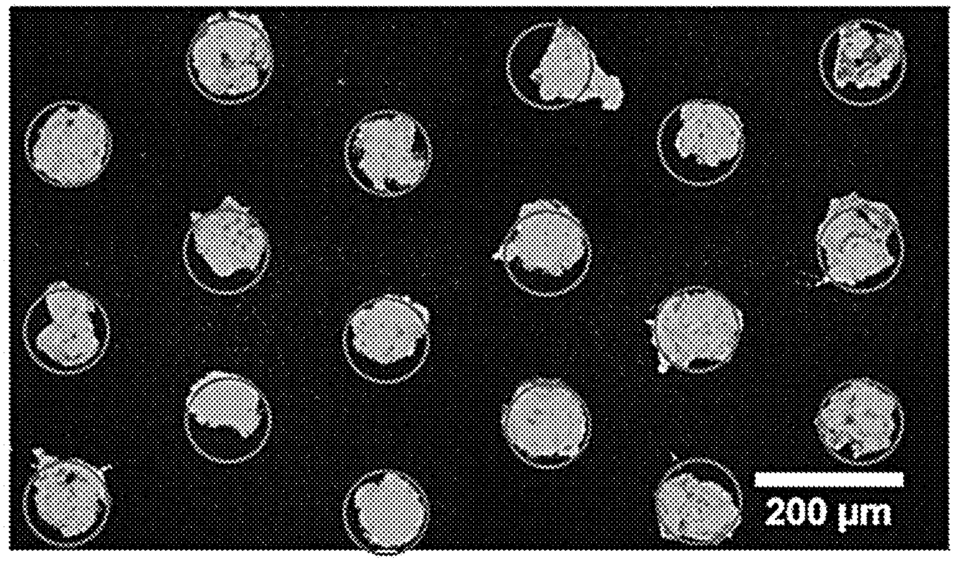
Figure 16:
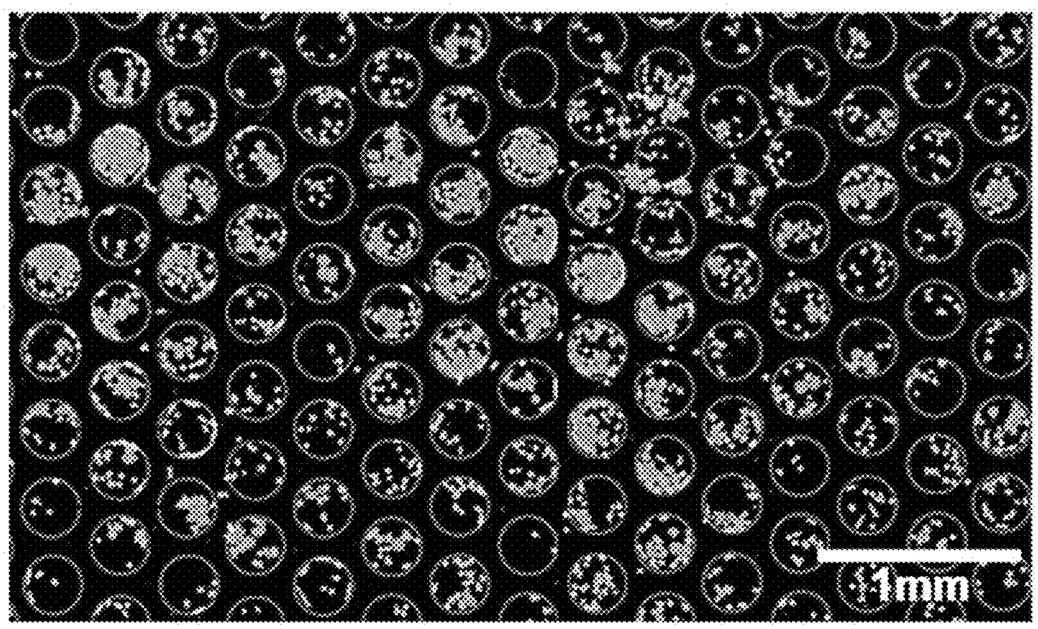
FIG. 16 shows a fluorescence micrograph (300 μm patterns and [C]=1×) for assembled microdroplets containing living cells with the nuclei labeled with Hoechst (blue) and actin filaments labeled with phallotoxins (green).
Figure 17:
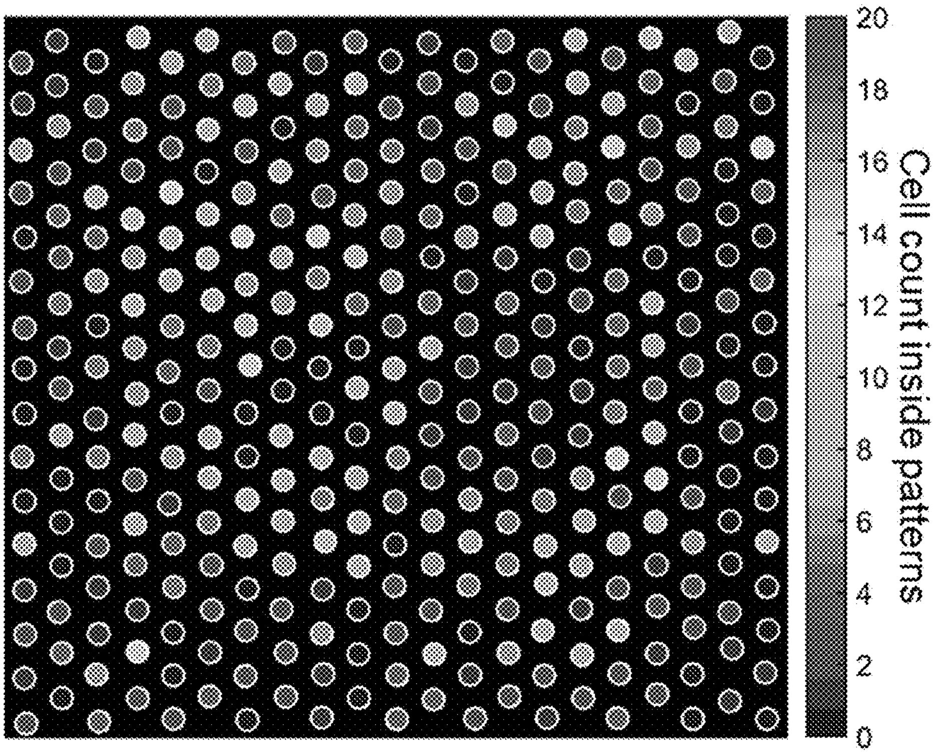
FIG. 17 shows a heat map for the cell counts in the fluorescence micrograph (125 um patterns and [C]=1×) provided at FIG. 15A.
Figure 18:
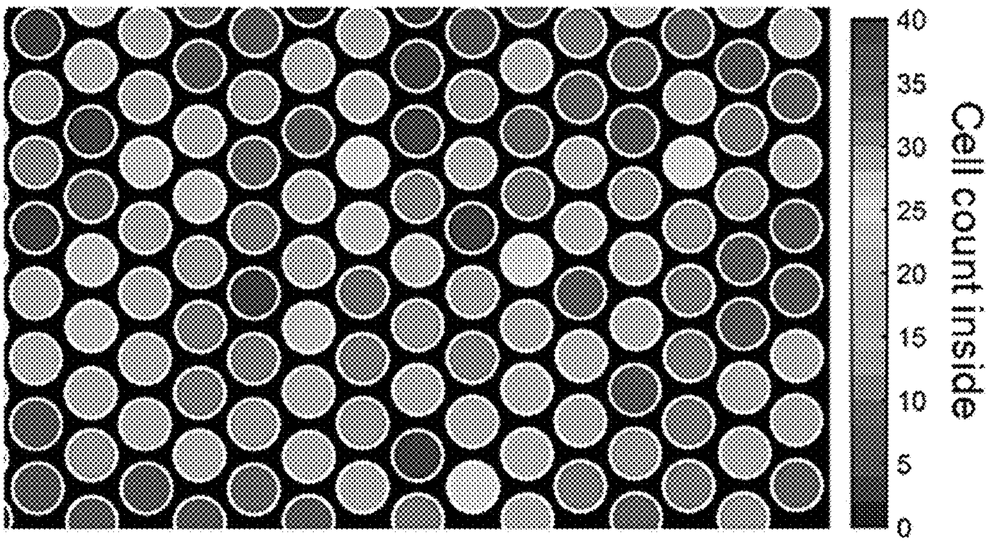
FIG. 18 shows a heat map for the cell counts in the fluorescence micrograph (300 um patterns and [C]=1×) provided at FIG. 16.
Figure 19:
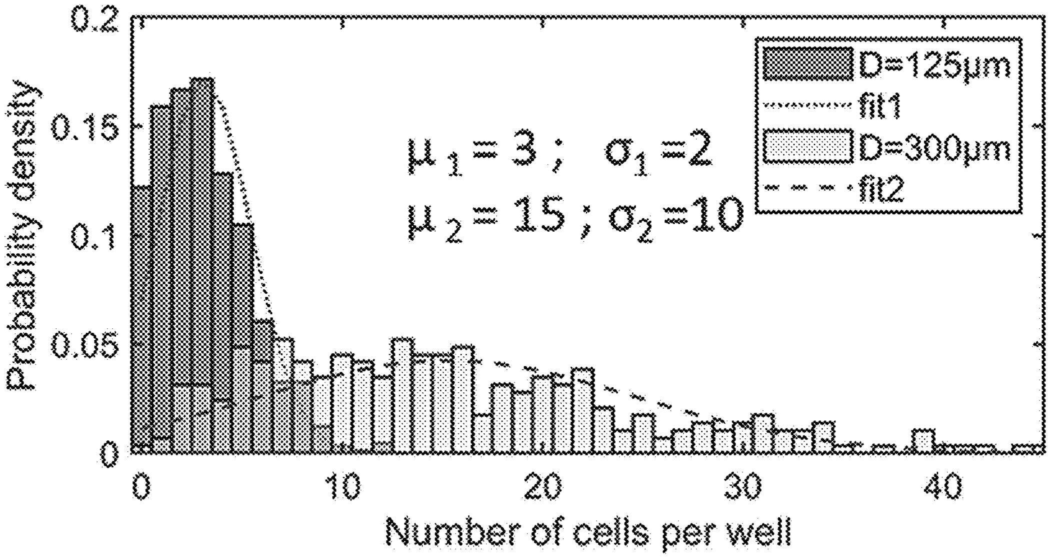
FIG. 19 shows the distribution of the number of cells per well for the fluorescence micrograph (125 μm patterns and [C]=1×) provided at FIG. 15A and the fluorescence micrograph (300 μm patterns and [C]=1×) provided at FIG. 16.

As evidenced by FIGS. 15A and 16, a regular array of cells with defined cell colonies inside each pattern was observed. Using the results set forth in FIGS. 15A and 16, heat color maps were generated to evaluate the homogeneity of the sample. The results are set forth in FIGS. 17 and 18, respectively. In addition, FIGS. 15A and 16 were used to evaluate the distribution of cells inside each pattern, and the results are set forth in FIG. 19.

An average of 3±2 cells per well was measured for samples with 125 μm patterns and 15±10 cells per well was measured for samples with 300 μm patterns, with a patterning efficiency higher than 85% (90% of patterns contain cells and 85% of all cells on the sample surface are inside the patterns).

Figure 20:
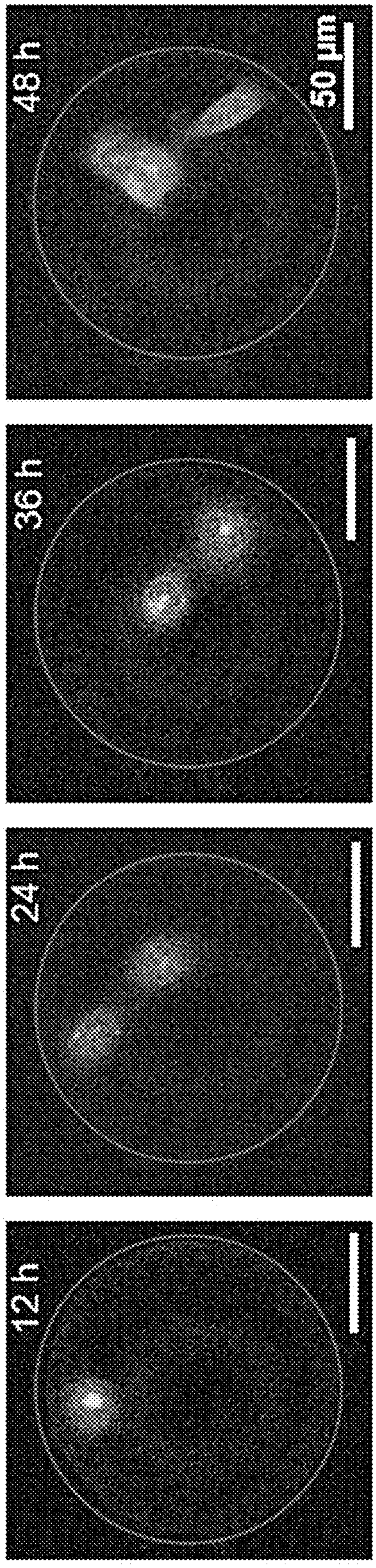
FIG. 20 shows a time-lapse image series of a single assembled colony with one cell labeled with CellTracker™ orange cultured for 48 hours with observation of every 12 hours.

The number of cells per well depended on the initial cell concentration and distribution after assembly, as well as the pattern size and incubation time (number of cell division cycles). Using a lower initial cell concentration, the attachment, growth, and division of a single cell within one colony was observed for a culture period of 48 h, and the results are set forth in FIG. 20. These results show that with proper control of cell density, arrays of monoclonal cells can be assembled.

Example 4

This example shows the effect on cell viability exhibited by a procedure for the generation of a micro-assembly of cells-in-droplets (μACD) that further includes alginate.

Figure 21:
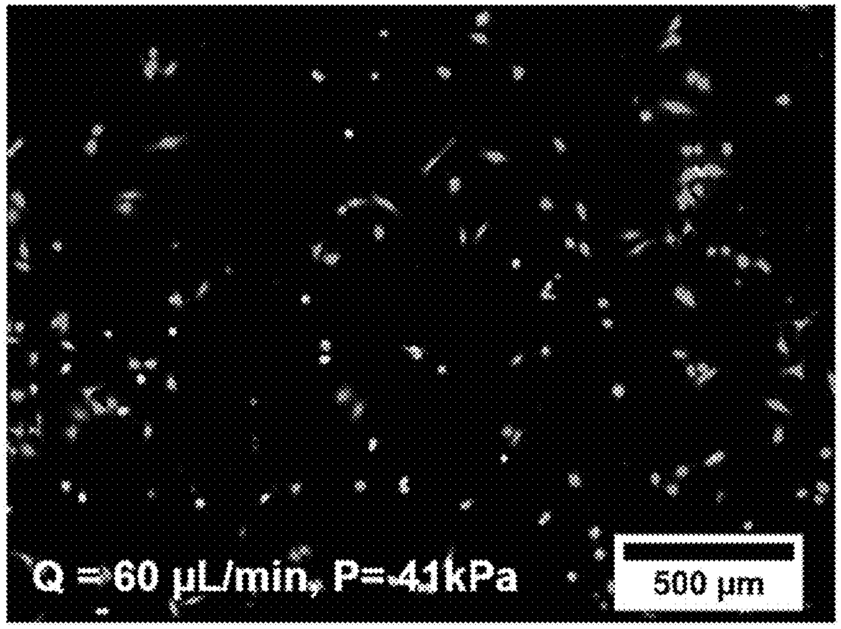
FIG. 21 shows a fluorescence micrograph of a live/dead assay of cells that have been sprayed using alginate (1%) in the cell suspension media onto plasma treated PDMS surfaces at 60 μL/min and 41 kPa and incubated in cell growth media for 24 hours. The live cells have been labeled with calcein-AM (green) and the dead cells have been labeled with propidium iodide (red).
Figure 22:
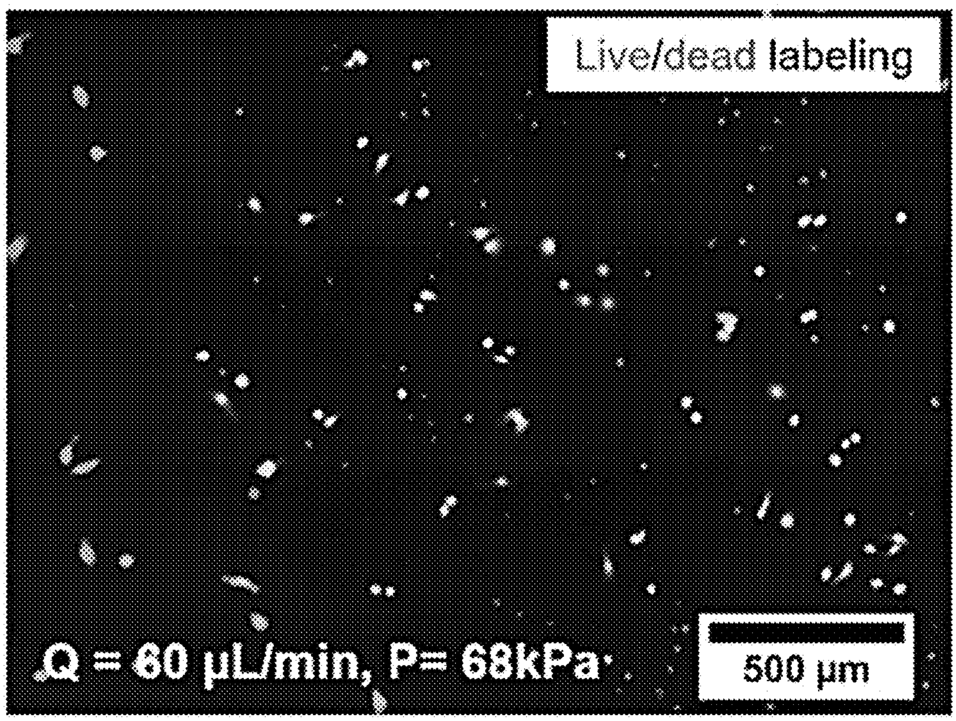
FIG. 22 shows a fluorescence micrograph of a live/dead assay of cells that have been sprayed using alginate (1%) in the cell suspension media onto plasma treated PDMS surfaces at 60 μL/min and 68 kPa and incubated in cell growth media for 24 hours. The live cells have been labeled with calcein-AM (green) and the dead cells have been labeled with propidium iodide (red).

Cells were sprayed using alginate (1%) in the cell suspension media onto plasma treated PDMS surfaces at (i) 60 μL/min and 41 kPa and (ii) 60 μL/min and 68 kPa and incubated in cell growth media for 24 hours. Fluorescence micrographs were generated for the live/dead assay of cells produced in (i) and (ii), and the results are set forth in FIGS. 21 and 22, respectively. The live cells were labeled with calcein-AM (green) and the dead cells were labeled with propidium iodide (red).

Figure 23:
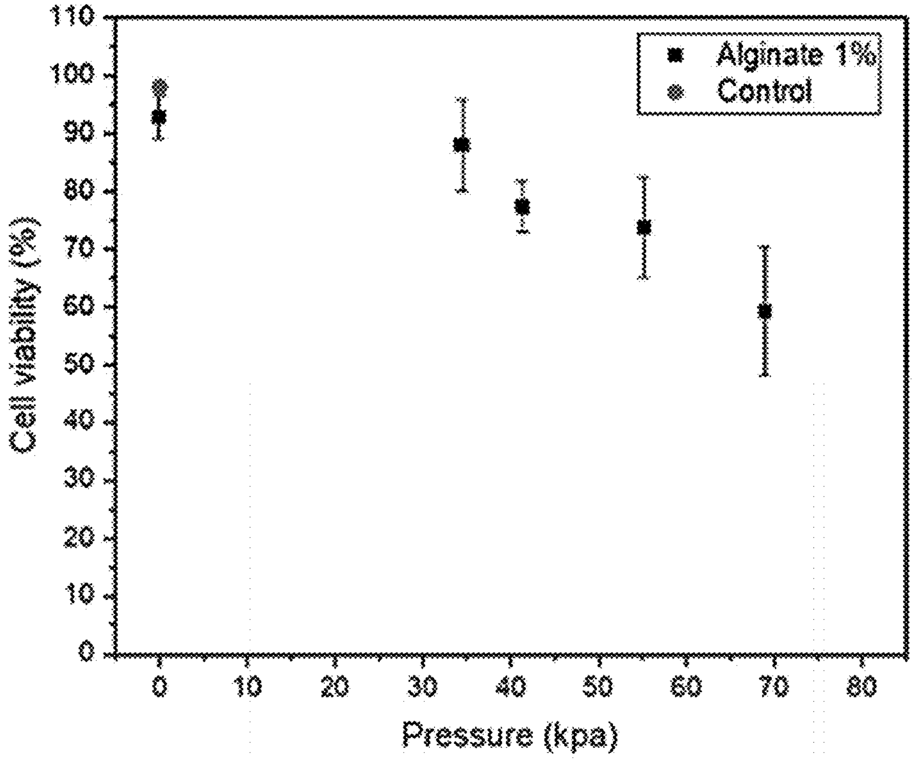
FIG. 23 provides a plot of the cell viability as a function of spraying pressure exhibited by cell that have been sprayed using alginate (1%) in the cell suspension media onto plasma treated PDMS surfaces.

Without wishing to be bound by any particular theory, it is believed that the thinning properties of alginate can reduce shear stress on cells during droplet formation and alleviate the induced shear upon impact of cells on a substrate. However, cell viability in alginate droplets was reduced as compared to experiments using cell culture media for the cell suspension, as evidenced by FIG. 23. It is believed that the foregoing effect could be explained by the extended processing times required for the cross-link of alginate liquid droplets with calcium chloride (100 mM), which is a diffusion driven process.

Example 5

This example demonstrates that the procedure for the generation of a micro-assembly of cells-in-droplets (μACD) can provide well-defined 2D surface patterns.

Figure 24:
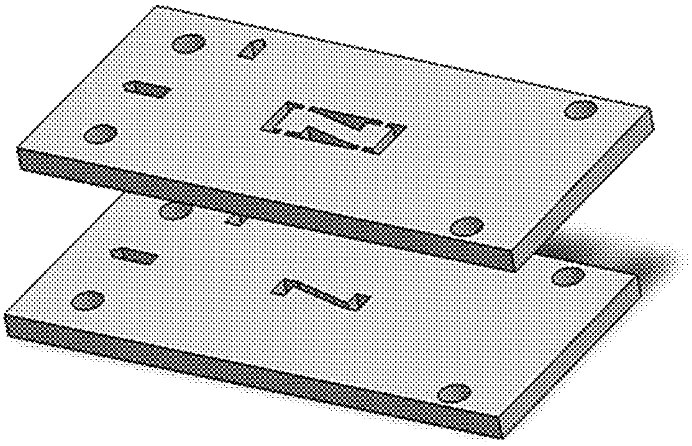
FIG. 24 shows an exemplary mask pattern for use in spray deposition.

A multi-step cell deposition procedure was performed using two unique shadow masks, as shown in FIG. 24, and A431 cells labeled with different dyes (CellTracker™ green and orange). As demonstrated by the fluorescence micrograph shown at FIG. 25, the resulting multi-cell array had the intended pattern, i.e., the Nebraska "N".

Figure 26:
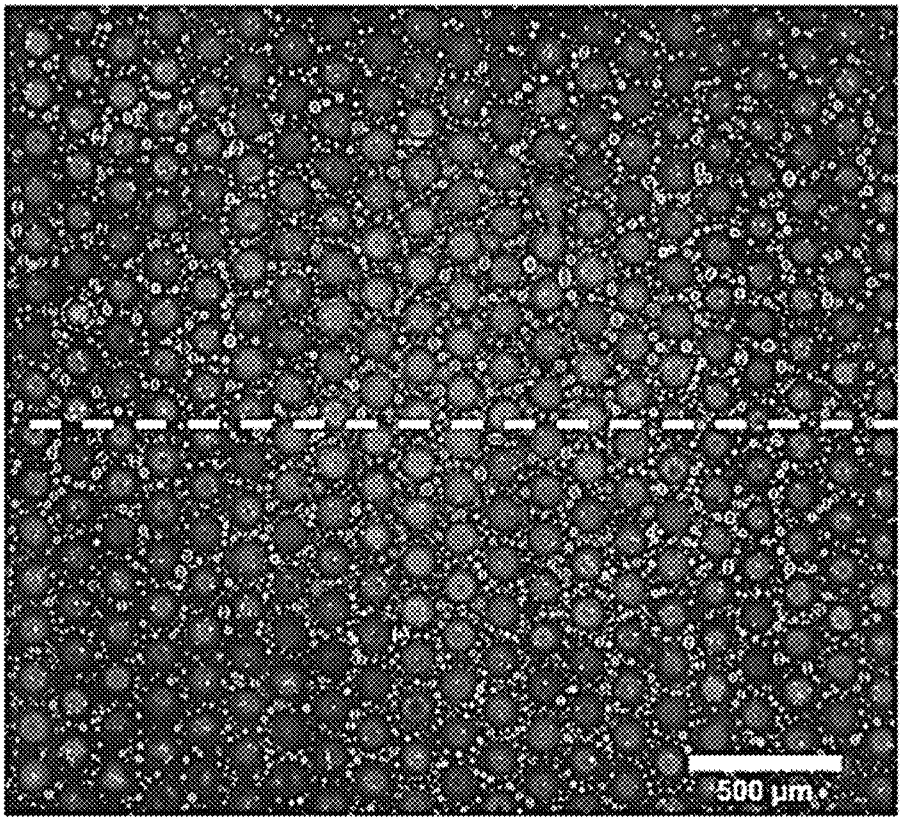
FIG. 26 shows a fluorescence micrograph showing concentric circles with A-431 cells stained with CellTracker™ green or CellTracker™ orange, assembled on elastomeric membranes containing 300 μm fluorescein isothiocyanate (FITC)-labeled poly-L-lysine (PLL) patterns.

Similarly, a multi-step cell deposition procedure was performed using two unique shadow masks to create concentric circles with A431 cells labeled with different dyes (CellTracker™ green and orange). The resulting concentric circles are shown in FIG. 26. In addition, FIG. 27 provides the cross-section fluorescence intensity levels for green and red channels extracted from the dotted white line shown in FIG. 26.

Figure 25:
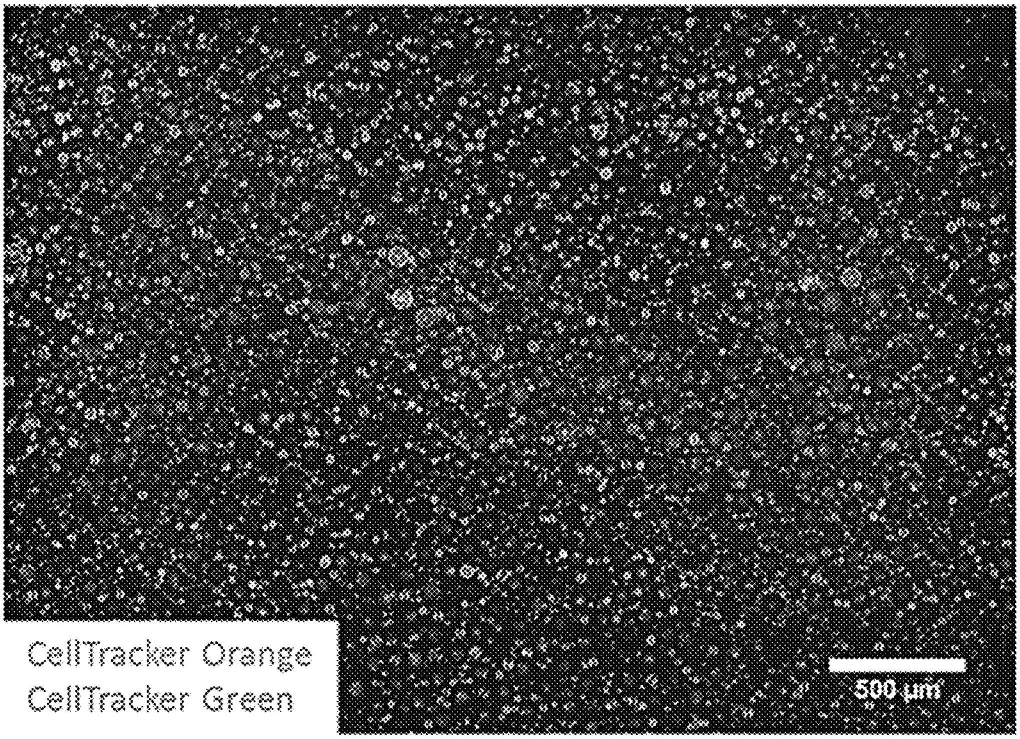
FIG. 25 shows a fluorescence micrograph showing the Nebraska "N" pattern with A-431 cells stained with CellTracker™ green or CellTracker™ orange, assembled on elastomeric membranes containing 300 μm fluorescein isothiocyanate (FITC)-labeled poly-L-lysine (PLL) patterns.
Figure 27:
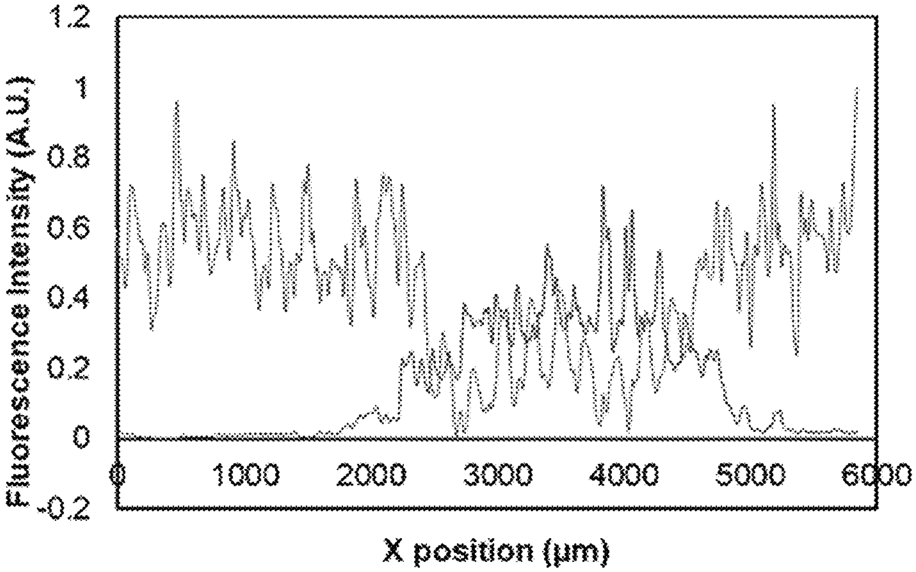
FIG. 27 provides the cross-section fluorescence intensity levels for green and red channels extracted from the dotted white line shown in FIG. 26.

As demonstrated by FIGS. 25-27, the inventive method forms distinct and well-defined 2D surface patterns.

Example 6

This example shows that μACD, as described in Example 2, can be used to generate patterned cell colonies from assembled 3D microdroplets in the preparation of micro-assembled organoids-in-gels (mAOG).

Figure 28:
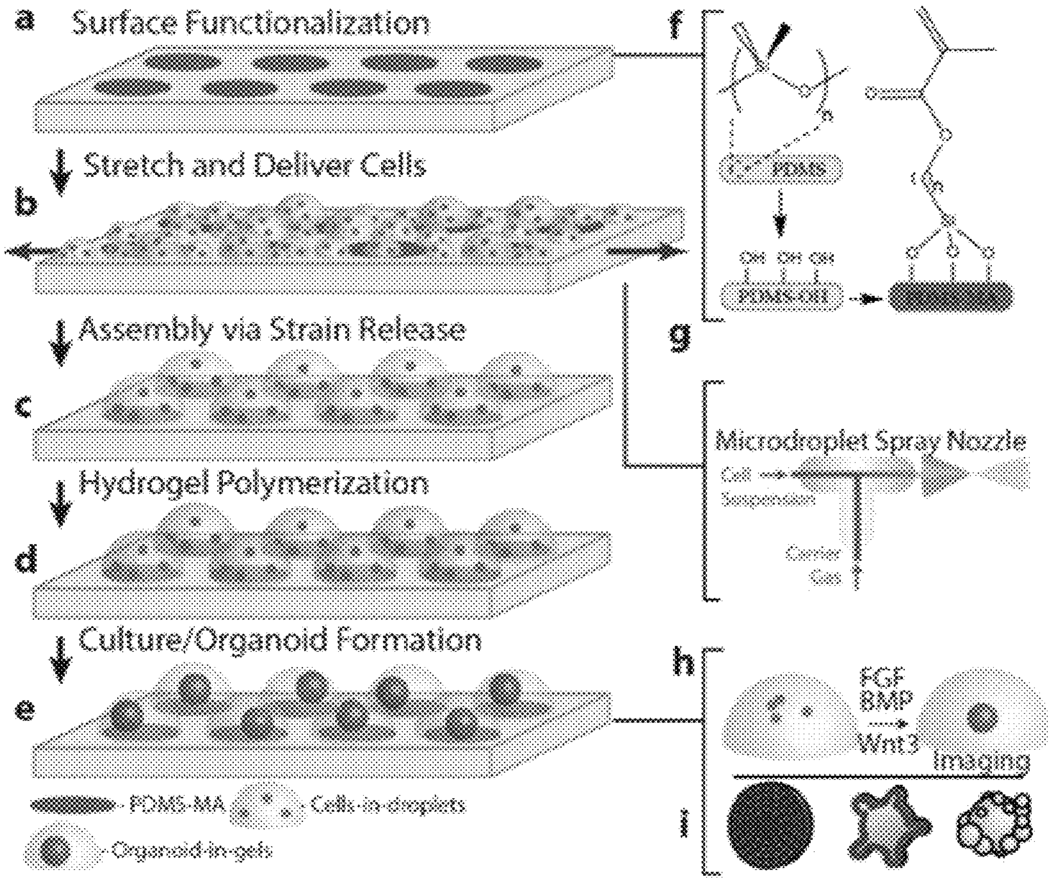
FIG. 28 is a schematic showing an exemplary preparation of a microassembly of organoids-in-gels. Surface-functionalized poly dimethylsiloxane (PDMS) supports with methacrylate linkers (a, f) are stretched and prepolymer cell suspensions are deposited in droplets using microdroplet spray nozzles or microdroplet emulsions (b, g). Strain release and assembly (c) is followed by gel crosslinking and surface coupling (d). Cell culture and growth factors induce organoid development and functional organoid-in-gels microarrays (e). Organoid formation can be induced via standard protocols (h), and the organoid arrays can be imaged for drug screening (i).

The mAOG procedure relies on the generation of stable wettability patterns that can assemble aqueous droplets based on the principles of wettability contrast, as shown in FIG. 28(*a, f*). Covalently modified poly(dimethylsiloxane) (PDMS, formulated using commercial Sylgard 184 kits) is used as the elastomeric substrate to form wettability patterns capable of controlling the hydrophobic and hydrophilic interactions with aqueous solutions (i.e., cell suspensions). The covalently modified PDMS wettability patterns (i) contain methacrylate coupling functionality for attaching the PEG hydrogels and (ii) are resistant to cell adhesion. Thus, methacrylate modified PDMS (PDMS-MA) surfaces are used because the surfaces support crosslinking to the PEG hydrogels (through both photo and chemical crosslinking procedures) and deter cell adhesion. For example, as shown in FIG. 28 (*f*), the PDMS surfaces are modified via vapor phase and/or solution phase deposition of 3-(trimethoxysilyl)propyl methacrylate following oxidation (with either UV ozone or oxygen plasma treatment).

As shown in FIG. 28, the surface-functionalized polydimethylsiloxane (PDMS) supports with methacrylate linkers (a, f) are stretched and prepolymer cell suspensions are deposited in droplets using microdroplet spray nozzles or microdroplet emulsions (b, g). Strain release and assembly (c) is followed by gel crosslinking and surface coupling (d). Cell culture and growth factors induce organoid development and functional organoid-in-gels microarrays (e). Organoid formation can be induced via standard protocols (h), and the organoid arrays can be imaged for drug screening (i).

Coaxial pneumatic micro-nozzles are used for compartmentalizing and delivering the different cell lines (e.g., cancer precursors, human colon carcinoma cells, HCT116, and induced pluripotent stem cells (iPSCs)) to the chemically patterned surfaces. Alternatively, flow-focusing droplet generators can be used to produce stable cell-in-droplet emulsions which can be transferred to the support substrates. In each case Matrigel™ precursor or cell culture media will be used in droplet generation.

Standard live/dead assays are used to efficiently assess the viability of cancer precursor cells and human induced pluripotent stem cells (iPSCs) in arrays in both liquid and Matrigel™ droplets. In particular, Calcein-AM (live cells) and Ethidium Homodimer-1 (EthD-1) (dead cells) staining is performed after 24 h, 48 h, 72 h of incubation. The potency of patterned iPSCs in liquid media and in Matrigel is monitored by staining pluripotency markers (Nanog, TRA-1-60 and SSEA4).

The PDMS-MA surfaces will provide the necessary wettability contrast to support assembly and to deter cell adhesion. The delivery of iPSCs using coaxial pneumatic micro-nozzles produces cell cultures with high viability (>90%) in both liquid and Matrigel based delivery methods. The patterned iPSCs are expected to maintain their pluripotency in liquid and Matrigel conditions after patterning.

Example 7

This example demonstrates that micro-assembled organoids-in-gels (mAOG) can be generated with designer scaffolds generated using synthetic microgels with highly tunable chemical and mechanical properties, which provide suitable microenvironments for organoids based on iPSCs and colon cancer cells.

Instead of using Matrigel, as described in Example 6, unique polyethylene glycol (PEG) hydrogels are prepared by varying crosslinker chemistry and modifying the main chain chemistry with appropriate peptide motifs (e.g., PEG-4MAL with cysteine-rich extracellular matrix motifs). In particular, a hydrogel prepolymer formulation is prepared using a hydrogel macromer, extracellular matrix modifier, and crosslinker, chosen from the structures shown in FIG. 29. Synthetic hydrogel (i.e., prepolymer formulations) suspensions of iPSCs and colon cancer cells are assembled into droplet arrays using the protocols described in Examples 2 and 6. The iPSCs and colon cancer cells are differentiated into gastrointestinal (GI) organoids via exposure to FGF and Wnt3 treatment and colorectal cancer (CRC) tumor organoids, respectively.

The PEG prepolymer formulations used in cell delivery for mAOG will have similar viscosities and are thus not expected to alter aerosol droplet formation. The PEG prepolymer formulations can be photo-crosslinked and/or chemically crosslinked to form chain growth (CG) and step growth (SG) networks, respectively (FIG. 29(*b, c*)). Photo-crosslinked CG networks are cured using light, and the network is heterogeneous in nature. In contrast, chemically crosslinked SG networks deliver homogenous networks with relatively regular morphologies. Both crosslinking strategies are compatible with the coaxial aerosol micro-droplet delivery procedures. Generally, the mechanics of the PEG hydrogel scaffolds will be controlled by varying macromer molecular weight (Mn), prepolymer concentration, and crosslinker density. To modify the PEG hydrogels, matrix modifiers (e.g., PEG-NHS and PEG-4Mal) can be incorporated into macromer stock solutions for modification with select extracellular matrix (ECM) proteins with reactive amine and cysteine functionality (FIG. 29(*d, e*)).

Exemplary extracellular matrix (ECM) based modifications for stem cell cultures include RGD, fibronectin, laminin-111, collagen IV, and hyaluronic acid. The PEG-NHS and PEG-4Mal modifiers are compatible with amine and cysteine rich ECM, respectively. Stiffness of the resulting hydrogel networks are measured using atomic force microscopy (AFM) nanoindentation and the chemical modifications are verified using matrix-assisted laser desorption/ionization (MALDI) and Fourier transform mass spectroscopy.

After the colon cancer cells are delivered to the elastomeric surface using the synthetic mechanically/chemically adapted hydrogels, the cell viability, assembly, and proliferation are monitored. Induction of CRC tumor organoid will be achieved by maintaining the gel-encapsulated cells in McCoy5a medium supplemented with Y27632 (10 μM) for three days.

Similarly, after the iPSCs are delivered to the elastomeric surface using the synthetic mechanically/chemically adapted hydrogels, the cell viability, assembly, and proliferation are monitored. Differentiation of iPSCs to GI organoids in the assembled hydrogel arrays will be achieved by exposing the iPSCs to CDM-PVA and activing-A (100 ng/ml), BMP (10 ng/ml), bFGF (20 ng/ml) and LY294002 (10 μM) after hydrogel droplet assembly for 3 days. Differentiated cells are maintained in media containing human EGF (100 ng/ml), R-spondin (500 ng/ml), Y-27632 (10 μM), Noggin (100 ng/ml), and human Wnt3a (100 ng/ml). Control experiments for the organoid arrays are carried out in petri dishes using Matrigel™ for iPSC differentiation and organoid formation. The organoids are characterized by co-staining with Lgr5 and Ki67.

The foregoing procedures generate microarrays of hydrogel-encapsulated CRC tumor organoids and iPSC-derived GI organoids by controlling the precursor cells, the chemistry and mechanics of the microgel scaffolds, and the specific growth factors used in culture. These microarrays represent the first high-throughput batch tumor organoids produced without the requirement of lithography and the associated perturbations. The CRC tumor organoid and iPSC-derived organoid arrays can be stabilized within substrate-supported hydrogel microenvironments suitable for long-term culture within batch reactors and microfluidic devices with active nutrient flow.

Example 8

This example demonstrates that micro-assembled organoids-in-gels (mAOG) of the invention can be used in image-based phenotypic analysis and drug screening assays as a testbed.

Using the micro-assembled organoids-in-gels (mAOG) techniques described in Examples 6 and 7, drug screening investigations are performed with designer PDMS microfluidic chips for sustainable maintenance and observation of the organoid microarrays. Media flow as well as chemical perturbations are programmed and carried out using low-flow pneumatic pumps within temperature-regulated incubators. These microfluidic devices are mechanically sealed (avoiding plasma of UV ozone sealing procedures that may harm cells), enabling analysis of the array for purposes such as drug screening.

Figure 30:
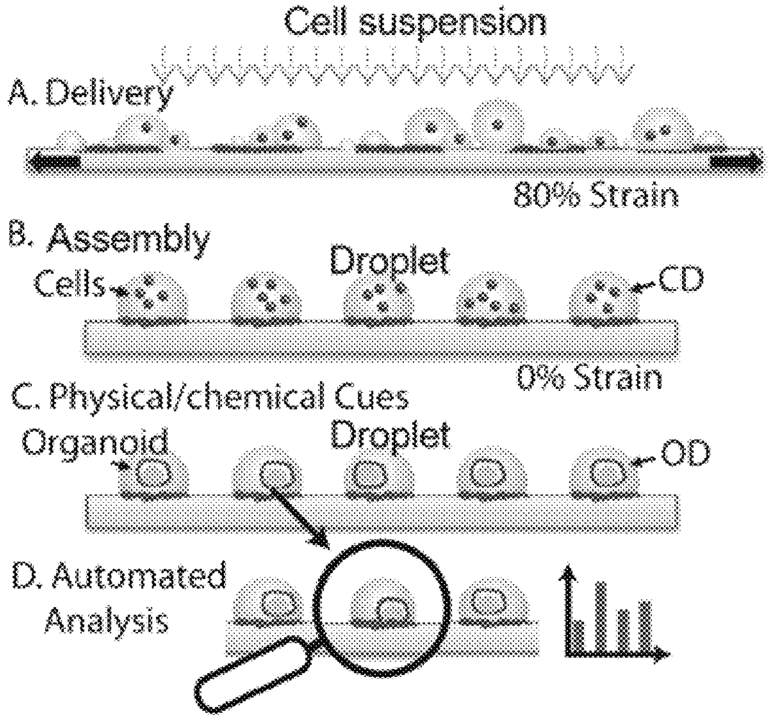
FIG. 30 is a schematic demonstrating the use of micro-assembled organoids-in-gels in automated drug screening. Micro-assembled organoids-in-gels are applied by aerosol-based delivery to the surface of an elastomeric substrate (A) and droplet coalescence and assembly is performed by applying strain (A, B). Organoid formation occurs using physical and/or chemical cues (C), and automated microarray analysis (e.g., drug screening) can be performed.

As shown in FIG. 30, micro-assembled organoids-in-gels are applied by aerosol-based delivery to the surface of an elastomeric substrate (A) and droplet coalescence and assembly is performed by applying strain (A, B). Organoid formation occurs using physical and/or chemical cues (C), and automated microarray analysis (e.g., drug screening) can be performed.

To demonstrate the potential of the patterned tumor organoid arrays as a model for high throughput drug screening, as a testbed study, the tumor organoids are subjected to different anti-cancer compounds and high-content imaging and analysis is used to categorize their effects in inducing morphological changes of the microtissue as well as in forcing cell death. Specifically, these drugs will include an Akt inhibitor, afuresertib, and widely used EGFR inhibitors, cetuximab and panitumumab, at 0.01 μM, 0.1 μM, 0.5 μM, 1 μM and 10 μM concentrations. DMSO is used as loading control. Imaging-based phenotypic analysis of Calcein-AM and EthD-1 stained tumor organoids is performed after 24 h, 48 h and 72 h of drug exposure. The captured images are analyzed using CellProfiler software. Features, including organoid area and mean intensities of Calcein-AM and EthD-1, are extracted post measurement and segmentation analysis of each tumor organoid within an array of 20 by 20 (the size that was established in our prior studies). These averaged feature values from each array of 400 organoids is plotted against the drug concentration and normalized against the DMSO control to produce the IC50 values for each compound. The experiment will be run in triplicate for each concentration and compared to the obtained IC50 values with benchmarks from in vitro studies. In other words, the three independent experiments with automated analysis of the 400 organoids from each (with reduced heterogeneity due to the uniformity of designer scaffolds) is sufficient to achieve the screening results of 1,200 separate assays and imaging analysis.

The efficacy of drugs and drug combination based on the phenotypical analysis results can be rapidly assessed with the micro-assembled organoids-in-gels (mAOG). The data can be compared to well-established in vitro studies using the same set of concentrations for validation. Without wishing to be bound by any particular theory, we believe that the increased number of organoids and the limited heterogeneity from the controlled tumor microenvironment will significantly reduce the uncertainty of the obtained efficacy data.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for preparing an ordered microarray, the method comprising process (A) or process (B):

(A) (i) providing an elastomeric substrate, (ii) modifying a surface of the elastomeric substrate thereby producing a surface-modified elastomeric substrate, (iii) spraying a composition onto the surface-modified elastomeric substrate thereby producing a disordered microarray, and (iv) applying a strain to the disordered microarray thereby producing the ordered microarray; or (B) (i) providing an elastomeric substrate, (ii) modifying a surface of the elastomeric substrate thereby producing a surface-modified elastomeric substrate, (iii) applying a strain to the surface-modified elastomeric substrate thereby producing a strained surface-modified elastomeric substrate, (iv) spraying a composition onto the strained surface-modified elastomeric substrate thereby producing a disordered microarray, and (v) relaxing the disordered microarray thereby producing the ordered microarray.

2. The method of claim 1, wherein modifying the surface of the elastomeric substrate of step (ii) of process (A) or step (ii) of process (B) comprises masking the elastomeric substrate and chemically modifying at least a portion of the surface of the elastomeric substrate thereby producing the surface-modified elastomeric substrate.

3. The method of claim 2, wherein the step of chemically modifying at least a portion of the surface of the elastomeric substrate provides at least a portion of the surface of the elastomeric substrate that enables assembly of a disordered microarray into an ordered microarray by hydrophobicity contrast and is capable of attachment of a chemical moiety by chemically, thermally, and/or photolytically treating the surface-modified elastomeric substrate in the ordered microarray.

4. The method of claim 2, wherein the step of chemically modifying at least a portion of the surface of the elastomeric substrate comprises oxidizing the surface.

5. The method of claim 2, wherein the step of chemically modifying at least a portion of the surface of the elastomeric substrate comprises attaching to the surface of the elastomeric substrate a peptide-based adhesion promoter, a small molecule adhesion promoter, a (meth)acrylate-containing compound, a (meth)acrylamide-containing compound, a polyethylene glycol-containing compound, a fluorocarbon, a NHS-ester-containing compound, a maleimide-containing compound, an azide-containing compound, an alkyne-containing compound, or any combination thereof.

6. The method of claim 2, wherein the composition is a cell-containing composition, the disordered microarray is a disordered cell-containing microarray, and the ordered microarray is an ordered cell-containing microarray.

7. The method of claim 6, wherein the step of chemically modifying at least a portion of the surface of the elastomeric substrate provides at least a portion of the surface of the elastomeric substrate that enables assembly of a disordered cell-containing microarray into an ordered cell containing microarray by hydrophobicity contrast and promotes cell adhesion or is capable of attachment of a chemical moiety by chemically, thermally, and/or photolytically treating the surface-modified elastomeric substrate in the ordered cell-containing microarray.

8. The method of claim 1, wherein the composition is sprayed at a pressure of about 5 kPa to about 100 kPa.

9. The method of claim 1, wherein the composition is sprayed at a flow rate of about 10 $\mu Lmin^{-1}$ to 100 $\mu Lmin^{-1}$.

10. The method of claim 1, wherein the composition is sprayed at a distance of about 1 cm to about 20 cm from the surface-modified elastomeric substrate or the strained surface-modified elastomeric substrate.

11. The method of claim 1, wherein applying the strain to the disordered microarray of step (iv) of process (A) or the surface-modified elastomeric substrate of step (iii) of process (B) comprises stretching the elastomeric substrate uniaxially, biaxially, or omnidirectionally.

12. The method of claim 1, wherein the composition is a cell-containing composition, the disordered microarray is a disordered cell-containing microarray, and the ordered microarray is an ordered cell-containing microarray.

13. The method of claim 12, wherein the method further comprises attaching the cell-containing composition to the surface-modified elastomeric substrate in the ordered cell-containing microarray by chemically, thermally, and/or photolytically treating the surface-modified elastomeric substrate in the ordered cell-containing microarray.

14. The method of claim 12, wherein the method further comprises transferring the ordered cell-containing microarray to a cell culture media and inducing and/or sustaining growth of a cell.

15. The method of claim 12, wherein the cell-containing composition comprises somatic cells, stem cells, or a combination thereof.

16. The method of claim 1, wherein the elastomeric substrate comprises a silane-based material.

* * * * *